United States Patent
Wang et al.

(10) Patent No.: US 12,427,181 B2
(45) Date of Patent: Sep. 30, 2025

(54) T-CELL THERAPY METHOD

(71) Applicants: IMMUNOTECH BIOPHARM CO., LTD., Beijing (CN); PHAROS VACCINE INC., Gyeonggi-do (KR); NATIONAL INSTITUTES FOR FOOD AND DRUG CONTROL, Beijing (CN)

(72) Inventors: Yu Wang, Beijing (CN); Hyunsoo Lee, Gyeonggi-do (KR); Namchul Jung, Gyeonggi-do (KR); Youchun Wang, Beijing (CN); Lei Sun, Beijing (CN); Qiang Liu, Beijing (CN); Yonghua Zhang, Beijing (CN); Meng Wang, Beijing (CN)

(73) Assignees: Immunotech Biopharm Co., Ltd., Beijing (CN); Pharos Vaccine Inc., Gyeonggi-do (KR); National Institutes for Food and Drug Control, Beijing (CN)

( * ) Notice: Subject to any disclaimer, the term of this patent is extended or adjusted under 35 U.S.C. 154(b) by 1281 days.

(21) Appl. No.: 17/051,410

(22) PCT Filed: Apr. 28, 2019

(86) PCT No.: PCT/CN2019/084773
§ 371 (c)(1),
(2) Date: Oct. 28, 2020

(87) PCT Pub. No.: WO2019/206326
PCT Pub. Date: Oct. 31, 2019

(65) Prior Publication Data
US 2021/0236549 A1     Aug. 5, 2021

(30) Foreign Application Priority Data

Apr. 28, 2018  (CN) .......................... 201810400248.5

(51) Int. Cl.
| | | |
|---|---|---|
| A61K 40/11 | (2025.01) | |
| A61K 38/17 | (2006.01) | |
| A61K 40/31 | (2025.01) | |
| A61K 40/42 | (2025.01) | |
| A61P 35/00 | (2006.01) | |
| C07K 16/28 | (2006.01) | |
| C12N 5/0783 | (2010.01) | |
| A61K 39/00 | (2006.01) | |

(52) U.S. Cl.
CPC ........ *A61K 38/177* (2013.01); *A61K 38/1774* (2013.01); *A61K 40/11* (2025.01); *A61K 40/31* (2025.01); *A61K 40/4211* (2025.01); *A61P 35/00* (2018.01); *C07K 16/2803* (2013.01); *C12N 5/0638* (2013.01); *A61K 2039/505* (2013.01); *A61K 2039/545* (2013.01); *A61K 2239/13* (2023.05); *C07K 2317/622* (2013.01)

(58) Field of Classification Search
None
See application file for complete search history.

(56) References Cited

FOREIGN PATENT DOCUMENTS

WO    WO-2019206326 A1    10/2019

OTHER PUBLICATIONS

Buonaguro et al (Clin. Vacc. Immunol. 2011, 18(1): 23-34) (Year: 2011).*
Repana et al (Genome Biol. 2019, 20: 1-12) (Year: 2019).*
HLA Nomenclature, 2023, 2 pages (Year: 2023).*
Wieczorek et al (Front. Immunol. 2017, 8, article 292: 1-16) (Year: 2017).*
Lieu et al (MHC Complex interaction with Peptides. IN: 3LS, John Wiley & Sons, Ltd, Chichester, DOI: 10.1002/9780470015902. a000922.pub2, 2011, pp. 1-12) (Year: 2011).*
Ramakrishna et al (Expert Opinion on Biological Therapy, 2020, 20(5): 503-516) (Year: 2020).*
Daga and Davila (Mol. Therapy-Oncolytics , 2016, 3, 16014, pp. 1-7) (Year: 2016).*
Kalos et al. (2011). "T Cells with Chimeric Antigen Receptors Have Potent Antitumor Effects and Can Establish Memory in Patients with Advanced Leukemia." Sci Transl Med, vol. 3, No. (95), pp. 95ra73-95ra73.
Xi et al. (2015). "Survivin and PSMA Loaded Dendritic Cell Vaccine for the Treatment of Prostate Cancer." Biol. Pharm, vol. 38, No. (6), pp. 827-835.
International Search Report mailed on Aug. 8, 2019, for PCT Application No. PCT/CN2019/084773, 3 pages, English translation.
Written Opinion mailed on Aug. 8, 2019, for PCT Application No. PCT/CN2019/084773, 6 pages, English language translation.
Beasley et al. (1983). Prevention of perinatally transmitted hepatitis B virus infections with hepatitis B immune globulin and hepatitis B vaccine. The Lancet. Nov. 12, 1983;322(8359):1099-1102.
Berger, C. et al., "Adoptive transfer of effector CD8+ T cells derived from central memory cells establishes persistent T cell memory in primates," The Journal of Clinical Investigation, Dec. 3, 2007, 118(1): 294-305.
Bonifant et al. (2016). Toxicity and management in CAR T-cell therapy. Molecular therapy oncolytics, 3: 16011 (7 pages total).
Brentjens, R. J., et al., "Safety and persistence of adoptively transferred autologous CD19-targeted T cells in patients with relapsed or chemotherapy refractory B-cell leukemias", Blood, The Journal of the American Society of Hematology (2011); 118(18): 4817-4828.

(Continued)

*Primary Examiner* — Misook Yu
*Assistant Examiner* — Marianne Dibrino
(74) *Attorney, Agent, or Firm* — COOLEY LLP

(57) ABSTRACT

The present invention belongs to the field of biomedicine. Specifically, the present invention relates to an improved T-cell therapy. More specifically, the present invention relates to enhancing the cancer treatment efficacy of therapeutic T cells (such as CAR-T or TCR-T cells) through stimulation with living cells expressing cancer-related antigens.

17 Claims, 16 Drawing Sheets
Specification includes a Sequence Listing.

(56) References Cited

OTHER PUBLICATIONS

Cherkassky, L. et al. (2016). Human CAR T cells with cell-intrinsic PD-1 checkpoint blockade resist tumor-mediated inhibition, J. Clin. Invest. 126:3130-3144.

Chmielewski, M. et al. (May 18, 2015) "TRUCKs: the fourth generation of CARS" Exp Opin Biol Ther, 15(8):1145-1154.

Chun et al. (2002). "Relationship between the Size of the Human Immunodeficiency Virus Type 1 (HIV-1) Reservoir in Peripheral Blood CD4+ T Cells and CD4+: CD8+ T Cell Ratios in Aviremic HIV-1-Infected Individuals Receiving Long-Term Highly Active Antiretroviral Therapy." The Journal of Infectious Diseases 185.11: 1672-1676.

Curran et al. (2015). "How I treat acute lymphoblastic leukemia in older adolescents and young adults." Blood, The Journal of the American Society of Hematology 125.24: 3702-3710.

Davila et al. (2014). Efficacy and toxicity management of 19-28z CAR T cell therapy in B cell acute lymphoblastic leukemia. Science Translational Medicine, 6(224): 224ra225 (23 pages total).

Day et al. (2013). Lessons learned from HIV vaccine clinical efficacy trials. Current HIV Research, 11(6): 441-449.

Forman et al. (2013). "The myth of the second remission of acute leukemia in the adult." Blood, 121(7): 1077-1082.

Geyer et al. (2016). Review: Current clinical applications of chimeric antigen receptor (CAR) modified T cells. Cytotherapy, 18(11): 1393-1409.

Grada, Z. et al., "TanCAR: A Novel Bispecific Chimeric Antigen Receptor for Cancer Immunotherapy," Molecular Therapy—Nucleic Acids, 2, e105, doi:10.1038/mtna.2013.32 (2013) (11 total pages).

Grupp, S.A. et al., "Chimeric antigen receptor-modified T cells for acute lymphoid leukemia", N Engl J Med. (2013); 368(16): 1509-1518.

Gust et al. (2017). Endothelial Activation and Blood-Brain Barrier Disruption in Neurotoxicity after Adoptive Immunotherapy with CD19 CAR-T Cells. Cancer Discov, 7(12): 1404-1419.

Kneissl et al. (2013). "CD19 and CD20 targeted vectors induce minimal activation of resting B lymphocytes." PloS one 8.11: e79047 (10 pages total).

Kochenderfer et al. (2015). Chemotherapy-refractory diffuse large B-cell lymphoma and indolent B-cell malignancies can be effectively treated with autologous T cells expressing an anti-CD19 chimeric antigen receptor. Journal of clinical oncology; Official Journal of the American Society of Clinical Oncology, 33(6): 540-549.

Lee et al. (2015). "T cells expressing CD19 chimeric antigen receptors for acute lymphoblastic leukaemia in children and young adults: a phase 1 dose-escalation trial." The Lancet 385.9967: 517-528.

Lee et al. "Current concepts in the diagnosis and management of cytokine release syndrome", Blood, The Journal of the American Society of Hematology, (2014); 124(2):188-195.

Lewis et al. (2014). Antibody persistence and T-cell balance: two key factors confronting HIV vaccine development. Proceedings of the National Academy of Sciences of the United States of America, 111(44): 15614-15621.

Loos et al. (1976). A method for the recognition and separation of human blood monocytes on density gradients. Blood, 48(5): 731-742.

Maude Shannon L. et al. "Chimeric Antigen Receptor T Cells for Sustained Remissions in Leukemia" N Engl J Med. Oct. 16, 2014;371(16):1507-17.

Morgan RA et al., "Case Report of a Serious Adverse Event Following the Administration of T Cells Transduced with a Chimeric Antigen Receptor Recognizing Erbb2," Molecular Therapy 18(4):843-851 (2010).

Park et al. (2016). CD19-targeted CAR T-cell therapeutics for hematologic malignancies: interpreting clinical outcomes to date. Blood, 127(26): 3312-3320.

Park, J. H. et al., "Long-Term Follow-up of CD19 CAR Therapy in Acute Lymphoblastic Leukemia," The New England Journal of Medicine, Feb. 1, 2018, 378(5): 449-459.

Porter, D. L. et al., "Chimeric antigen receptor T cells persist and induce sustained remissions in relapsed refractory chronic lymphocytic leukemia," Science Translational Medicine, Sep. 2, 2015, 7(303): 303ra139; 12 pages.

Porter et al. (2011). Chimeric antigen receptor-modified T cells in chronic lymphoid leukemia. The New England journal of medicine, 365(8): 725-733.

Riddell et al., "Adoptive therapy with chimeric antigen receptor-modified T cells of defined subset composition," Cancer J. Mar.-Apr. 2014;20(2):141-144.

Ruella et al. (2016). Dual CD19 and CD123 targeting prevents antigen-loss relapses after CD19-directed immunotherapies. J Clin Invest, 126(10): 3814-3826.

Sommermeyer et al. (2016). Chimeric antigen receptor-modified T cells derived from defined CD8+ and CD4+ subsets confer superior antitumor reactivity in vivo. Leukemia, 30(2): 492-500.

Sotillo et al. (2015). Convergence of Acquired Mutations and Alternative Splicing of CD19 Enables Resistance to CART-19 Immunotherapy. Cancer Discov, 5(12): 1282-1295.

Trepo et al. (2014). Hepatitis B virus infection. The Lancet. 384(9959):2053-2063.

Turtle, C. J. et al., "CD19 CAR-T cells of defined CD4+:CD8+ composition in adult B cell ALL patients," The Journal of Clinical Investigation, Apr. 25, 2016, 126(6): 2123-2138.

Turtle, C.J. et al. (2016). Immunotherapy of non-Hodgkin lymphoma with a defined ratio of 08+ and CD4+ CD19-specifio chimeric antigen receptor-modified T Cells, Sci. Transl. Med. 8:355ra116. p. 1-13.

Wang et al. (2011). Engraftment of human central memory-derived effector CD8+ T cells in immunodeficient mice. Blood, 117(6): 1888-1898.

\* cited by examiner

A

B

A

B

A

B

A

B

T-CELL THERAPY METHOD

CROSS-REFERENCE TO RELATED APPLICATIONS

This application is a U.S. National Phase of International Application No. PCT/CN2019/084773, filed Apr. 28, 2019, which claims the benefit of priority to Chinese Application No. 201810400248.5, filed on Apr. 28, 2018, the entire contents of each of which are hereby incorporated by reference in their entirety.

REFERENCE TO AN ELECTRONIC SEQUENCE LISTING

The contents of the electronic sequence listing (NTDU-002_00US_corrected_sequence_listing.txt; Size: 7,309 bytes; and Date of Creation: Feb. 20, 2025) are herein incorporated by reference in its entirety.

TECHNICAL FIELD

The present invention belongs to the field of biomedicine. Specifically, the present invention relates to an improved T-cell therapy. More specifically, the present invention relates to enhancing the cancer treatment efficacy of therapeutic T cells (such as CAR-T or TCR-T cells) through stimulation with living cells expressing cancer-related antigens.

BACKGROUND OF THE INVENTION

At present, for children with B-cell acute lymphoblastic leukemia (B-ALL), multi-drug chemotherapy and/or targeted therapy have achieved a high complete remission rate, but still have a poor prognosis in adults and relapse/refractory B-ALL is a big challenge for all patients. Lymphocyte depletion chemotherapy followed by CD19-targeted chimeric antigen receptor-modified T (CAR-T) cell therapy is a new type of treatment, and it has been proven that the new treatment method has a strong response in in adults and children with relapsed/refractory B-ALL, chronic lymphocytic leukemia and lymphoma. New data from these studies indicate that the delivered significantly small doses of CAR-T cells can eliminate a large disease burden. However, long-term follow-up shows that the remission of most patients cannot be sustained. Due to poor persistence of CAR-T cells, CD19-positive tumors will recur. Therefore, it is currently believed that prolonging the existence of functional CAR-T cells in the body may be important for maintaining sustained remission.

A CAR generally contains an extracellular antigen binding domain (single chain variable fragment (scFV) of a monoclonal antibody) and an intracellular signaling domain that activates T cells. Genetically engineered CAR-T cells are highly effective against antigen-positive tumor cells in a major histocompatibility complex (MHC) independent manner. Currently, researchers are committed to seeking ways to improve the performance of CAR-T cells. One of the feasible methods is to modify the structure of the CAR, such as the application of the second or third generation or even the fourth generation CAR, which combines the activation signal domain and the costimulatory signal domain, and can improve the expansion and persistence of T cells. After in-vitro expansion and adoptive infusion, CAR-T cells derived from different T cell subpopulations have different capabilities to proliferate and sustain in vivo. Compared with CD19-targeted CAR-T cells prepared based on effector memory T cells, CD19-targeted CAR-T cells prepared from purified naive T cells or central memory T cells are more effective in eliminating CD19+ tumors. In addition, the synergistic enhancement of efficiency can be achieved by delivering CAR-T cells derived from CD8/CD4 T cells with a determined ratio. The CAR-T cells currently in use retain the endogenous T cell receptor (TCR), and the biology of TCR and CAR crosstalk is very complicated. The concomitant activation of CAR and TCR greatly weakens the in-vivo efficacy of CD8+CAR-T cells. On the contrary, CD4+ CAR-T cells maintain their capability to survive in vivo in the presence of TCR and CAR antigens.

Although the development of new CAR structures and the precise determining of the source of CAR-T cells may help to improve the application of CAR-T, these strategies cannot fundamentally promote the generation of CAR-T cells' immune memory, which is necessary for adaptive immune response. Moreover, repeated administration of CAR-T cells tends to induce immune clearance against those engineered T cells. Therefore, in the art, there is still a need for new CAR-T cell therapy strategies, especially strategies that can induce CAR-T cell immune memory.

SUMMARY OF THE INVENTION

In a first aspect, the present invention provides a method of treating cancer in a subject, including the following steps:
(a) administering therapeutic T cells specifically targeting a cancer-related antigen to the subject; and
(b) administering cells expressing the cancer-related antigen to the subject.

In a second aspect, the present invention provides a method for preventing cancer progression or recurrence in a subject, where the subject has undergone cancer treatment using therapeutic T cells specifically targeting a cancer-related antigen, the method including administering cells expressing the cancer-related antigen to the subject.

In a third aspect, the present invention provides a combination for treating cancer in a subject, which includes therapeutic T cells specifically targeting a cancer-related antigen and cells expressing the cancer-related antigen.

In a fourth aspect, the present invention provides the use of the combination of the third aspect of the present invention in the preparation of a medicament for treating cancer in a subject.

In a fifth aspect, the present invention provides the use of cells expressing a cancer-related antigen in the preparation of a medicament for treating cancer in a subject, where the medicament further includes therapeutic T cells that specifically target the cancer-related antigen.

In a sixth aspect, the present invention provides the use of cells expressing a cancer-related antigen in the preparation of a medicament for preventing cancer progression or recurrence in a subject, where the subject has undergone cancer treatment using therapeutic T cells specifically targeting the cancer-related antigen.

In a seventh aspect, the present invention provides the use of therapeutic T cells specifically targeting a cancer-related antigen in the preparation of a medicament for treating cancer in a subject, where the medicament further includes cells expressing the cancer-related antigen.

In an eighth aspect, the present invention provides cells expressing a cancer-related antigen, which are used in combination with therapeutic T cells that specifically target the cancer-related antigen to treat cancer in a subject.

In a ninth aspect, the present invention provides cells expressing a cancer-associated antigen for use in preventing cancer progression or recurrence in a subject, where the subject has undergone cancer treatment using therapeutic T cells that specifically target the cancer-related antigen.

In a tenth aspect, the present invention provides therapeutic T cells specifically targeting a cancer-related antigen, which are used in combination with cells expressing the cancer-related antigen to treat cancer in a subject.

In an eleventh aspect, the present invention provides a kit including therapeutic T cells specifically targeting a cancer-related antigen and/or cells expressing the cancer-related antigen, and the kit is used for treating cancer or preventing cancer progression or recurrence in the subject through the method of the present invention.

DETAILED DESCRIPTION OF THE INVENTION

Figure 1:
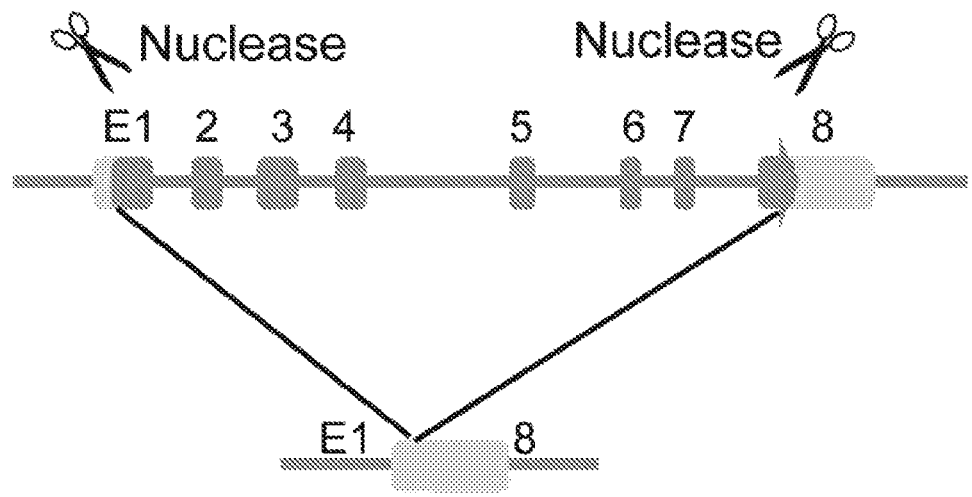
FIG. 1. Generation and characterization of B-NDG mice. (A) Schematic diagram of the Il2rg gene deletion targeting strategy through the CRISPR/Cas9 genome editing technology. (B) Detection of different lymphocyte populations in the peripheral blood and spleen of NOD-scid and B-NDG mice through flow cytometry. The number indicates the percentage of positive cells of a given phenotype. (C) 6-week-old C57BL/6, nude mice, Rag2−/−, NOD-scid and B-NSG mice were separately implanted with $5 \times 10^5$ Raji cells through tail vein injection. The relative level of bioluminescence is displayed in pseudo colors, with red and blue representing the strongest and weakest luminous fluxes. (D) The total flux at each time point is displayed and each data point represents the average value (n=10). (E) The Raji cell count recognized by CD19-FITC is shown as a graph recorded by the cell count. The correlation between Raji cell count and total flux is calculated by fitting a logarithmic curve, $R^2$=0.90. (F) B-NDG mice died on day 17 or 18, but other mice survived on day 30. (G) CD19 is highly expressed on the surface of Raji-Fluc cells, and the luminescence intensity of Fluc is positively correlated with the number of Raji-Fluc cells.
Figure 1:
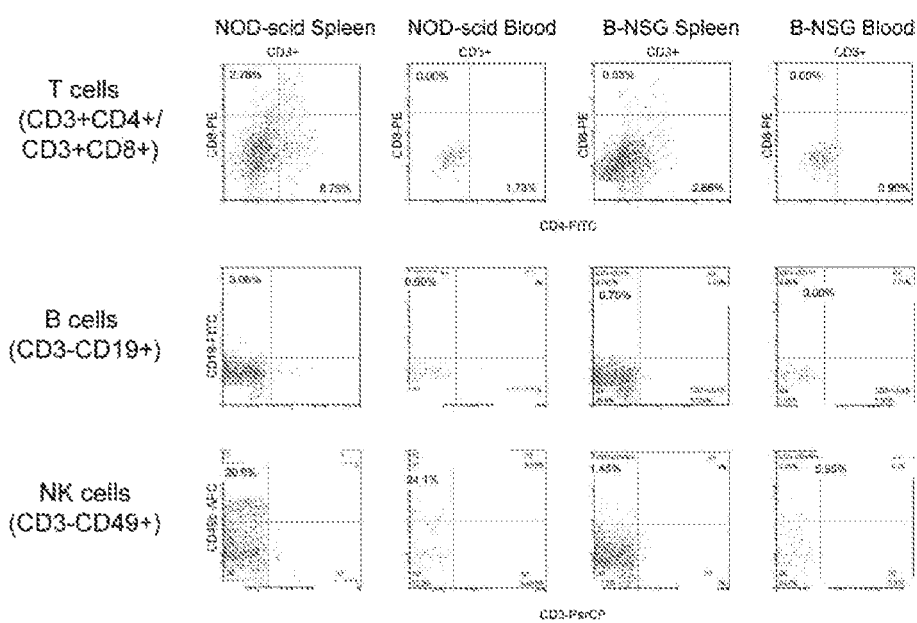
Figure 1:
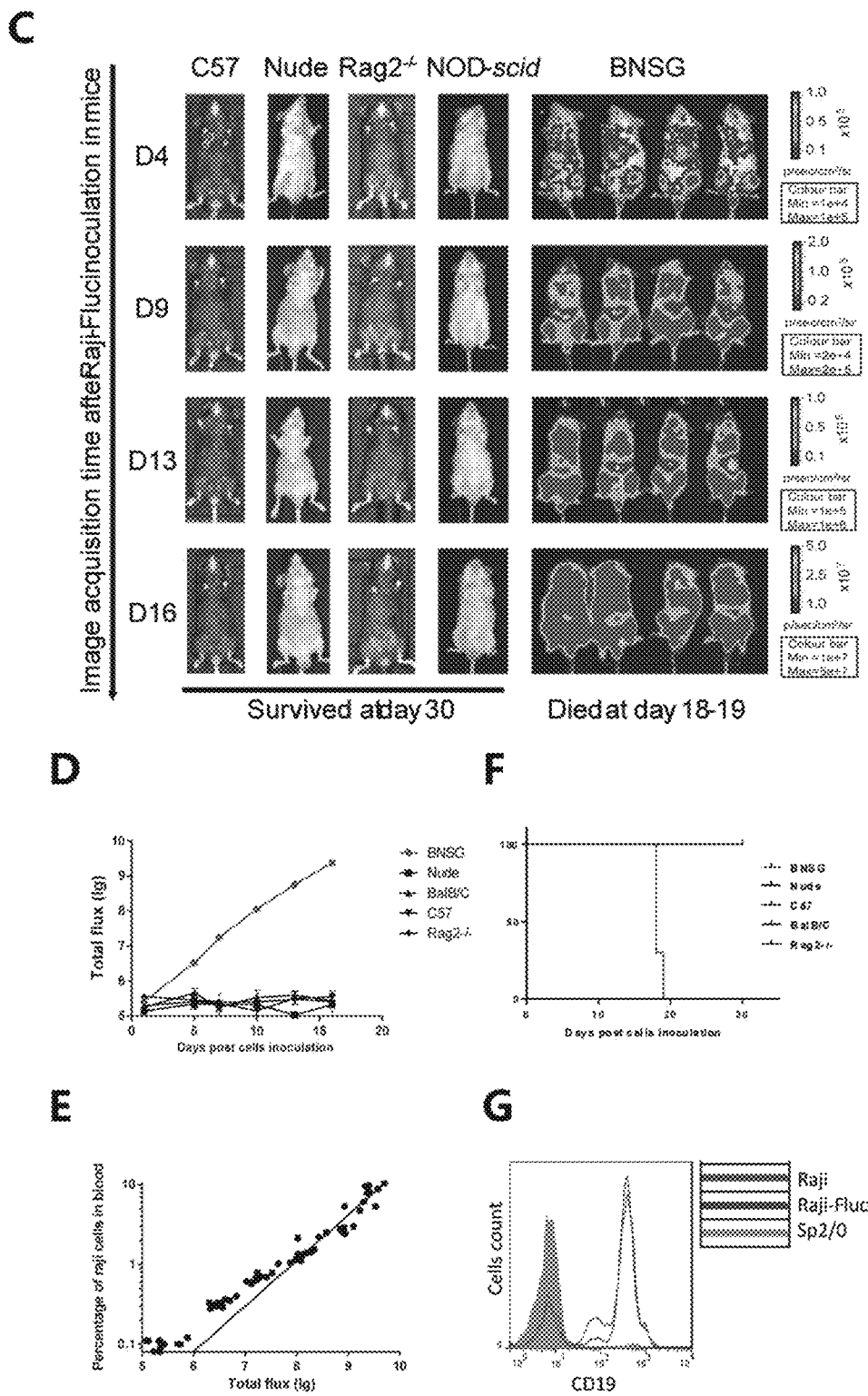

Unless otherwise indicated or defined, all the terms used have their usual meanings in the art, which will be understood by those skilled in the art. Reference is made to, for example, standard manuals such as Sambrook et al., "Molecular Cloning: A Laboratory Manual"; Lewin, "Genes VIII"; and Roitt et al., "Immunology" (Version 8), and general prior art cited in this specification. In addition, unless otherwise described, all methods, steps, technologies, and operations that are not specifically detailed can be and have been performed in a manner known per se, which will be understood by those skilled in the art. Reference is also made to, for example, the standard manual, the above-mentioned general prior art and other references cited therein.

Previous clinical trials have determined the effectiveness of CAR-T immunotherapy in cancer treatment, especially B-cell malignancies. The next step in treating cancer with CAR-T cells is to extend the duration of remission.

The remission rate of CAR-T treatment for CD19 in patients with relapsed/refractory B-ALL can reach 67% to 90%. However, the recurrence-free period only ranges from 2 months to 3 years. There are two recurrence modes after CD19 CAR-T treatment. One is the recurrence of CD19-positive tumors caused by insufficient persistence of CAR-T cells in vivo. The other is the recurrence caused by the loss of CD19-when CAR-T cells are present in vivo in about 20% of patients. Such loss may be caused by clonal selection or tumor evolution. Currently, researchers tend to inject additional CAR-T cells into patients when the CAR-T cells in the peripheral blood of the patients decrease or disappear, but the clinical effects of this approach vary greatly, indicating that the increase in CAR-T dose may not be the key to the persistence of CAR-T capability in vivo.

In the specific embodiments of the present invention, the inventors successfully constructed a Raji-B-NDG mouse model to study the efficiency of the CD19 CAR-T therapy. After treatment with CD19 CAR-T cells, mice in remission showed varying degrees of recurrence on day 20 (D20), and then died within D28 to D36, indicating that after initial exposure to antigens and elimination of tumor cells, the number of CAR-T cells injected gradually decreased, resulting in a final recurrence that could not be effectively controlled. The reason of recurrence may lie in the following two points. First, fluorescence detection in mice shows that the ideal tumor suppression effect is achieved only in organs with abundant blood flows (such as spleen and heart), but not effective in organs with fewer vascular branches (such as liver and brain), which indicates that the recurrence may come from these tissues. Secondly, the time of tumor recurrence is very important. Most PBMCs have a life span of less than 4 weeks. The in-vitro proliferation time of CAR-T cells up to 12 days before injection, plus the 20 days between injection and recurrence, is roughly the same as the 27-day life span of PBMCs. Therefore, the initial dose of CAR-T eliminates most of Raji cells, resulting in lack of antigen stimulation, and therefore proliferation is blocked and life span is consumed, and the number of CAR-T decreases until the tumor recurrence.

In order to maximize the specific killing effect of CAR-T, the problems of therapeutic cell life span and antigen stimulation should be solved in clinical applications. In the specific embodiments of the present invention, when D10 tumor cells have been basically eliminated by CAR-T, the effect of re-inoculation with tumor cells (Raji-Fluc) or cells expressing tumor antigens such as CD19 (such as T cells) is tested. Unexpectedly, compared with the single implantation group (tumor formation), the low-dose reimplantation group (re-stimulation) maintained a tumor-recurrence-free state for a longer time. More than half of the mice survived for more than 36 days, indicating that immune memory occurs under repeated stimulation of the same antigen, and rapid response to repeated injection of the same antigen leads to continuous suppression of tumor cells. Subsequently, the inventors studied whether antigens from Raji cells that died after irradiation can stimulate CAR-T cells. Unexpectedly again, the results show that reimplantation of dead tumor cells cannot awaken the memory of CAR-T cells, resulting in a short survival time for mice.

This indicates that CAR-T cells can only be activated by living cells carrying antigens. The inventors also surprisingly found that repeated administration of CAR-T therapy cannot delay tumor recurrence, which provides more evidence for the ineffectiveness of multiple CAR-T infusions. Without wishing to be limited by any theory, it is believed that the stimulation of low doses of living cells expressing cancer-related antigen can promote the generation of CAR-T cell immune memory, thereby leading to delayed recurrence and prolonged survival.

Therefore, in the first aspect, the present invention provides a method of treating cancer in a subject, including the following steps:
(a) administering therapeutic T cells specifically targeting a cancer-related antigen to the subject; and
(b) administering cells expressing the cancer-related antigen to the subject.

In some embodiments, the therapeutic T cells are administered one or more times, preferably once. In some embodiments, the cells expressing the cancer-related antigen are administered one or more times, preferably once.

In some embodiments, the cells expressing the cancer-related antigen are administered after the therapeutic T cells are administered. For example, the cells expressing the cancer-related antigens are administered about 1 day, about 2 days, about 3 days, about 4 days, about 5 days, about 6 days, about 7 days, about 8 days, about 9 days, about 10 days, About 11 days, about 12 days, about 13 days, about 14 days, about 15 days, about 16 days, about 17 days, about 18 days, about 19 days, about 20 days, or about 21 days after when the therapeutic T cells are administered.

In some embodiments, after administration of the therapeutic T cells reduces the cancer cell load, the cells expressing the cancer-related antigen are administered. For example, after the cancer cell load is reduced by at least about 5%, at least about 10%, at least about 20%, at least about 30%, at least about 40%, at least about 50%, at least about 60%, at least about 70%, at least about 80%, or at least about 90%, cells expressing the cancer-related antigen are administered. In some embodiments, after the cancer is completely remitted by administering the therapeutic T cells, the cells expressing the cancer-related antigen are administered. The change in cancer cell load in a subject can be determined by various methods known in the art. For example, for blood cancers, the cancer cell load can be determined by performing flow cytometry on circulating cells. In another example, for solid tumors, the tumor load can be determined by clinically commonly used imaging methods (such as MRI, CT, PET-CT, etc.). Alternatively, tumor load may be determined by detecting tumor markers. In some embodiments, before the cells expressing the cancer-related antigens are administered, the content of the therapeutic T cells may be detected to determine the change in tumor load, for example, the content of the therapeutic T cells is negatively correlated with the tumor load.

In some embodiments, after the therapeutic T cells are administered and when the amount of the therapeutic T cells in the subject decreases, the cells expressing the cancer-related antigen are administered. The amount of the therapeutic T cells in the subject can be detected by methods such as flow cytometry or quantitative PCR. For example, if the therapeutic T cells are CAR-T cells, the copy number of the CAR-encoding gene in the sample from the subject can be detected by PCR. When the copy number of the CAR-encoding gene decreases, cells expressing the cancer-related antigen are administered.

Therefore, in some embodiments, the method further includes the step of monitoring the tumor load and/or the amount of the therapeutic T cells in the subject after the therapeutic T cells are administered.

In some embodiments, after the therapeutic T cells are administered for one or more times, the cells expressing the cancer-related antigen are administered for one or more times. In some embodiments, after the therapeutic T cells are administered once, the cells expressing the cancer-related antigen are administered for one or more times. In some embodiments, the therapeutic T cells are administered for one or more times, and after each administration of the therapeutic T cells, the cells expressing the cancer-related antigen are administered for one or more times. In some embodiments, after the therapeutic T cells are administered once, the cells expressing the cancer-related antigens are administered once. In some embodiments, after the therapeutic T cells are administered, the cells expressing the cancer-related antigen are administered for one or more times. In some embodiments, after the therapeutic T cells are administered, the cells expressing the cancer-related antigen are administered once.

In some embodiments, the therapeutic T cells are administered in a therapeutically effective amount. As used herein, the therapeutically effective amount of therapeutic T cells refers to the amount of therapeutic T cells capable of reducing the load of cancer cells after use, for example, reducing the load of cancer cells by at least about 5%, at least about 10%, at least about 20%, at least about 30%, at least about 40%, at least about 50%, at least about 60%, at least about 70%, at least about 80%, at least about 90%, or a amount that completely remissions the cancer. In some embodiments of various aspects of the present invention, the effective amount of the therapeutic T cells is about $10^4$ to about $10^9$ cells, for example about $10^4$, about $10^5$, about $10^6$, about $10^7$, about $10^8$, or about $10^9$ cells. In some embodiments, the dose of therapeutic T cells is determined according to the body weight of the subject, for example, about $10^4$ cells/kg body weight to about $10^9$ cells/kg body weight, such as about $10^4$, about $10^5$, about $10^6$, about $10^7$, about $10^8$, or about $10^9$ cells/kg body weight.

In some embodiments, cells expressing cancer-related antigen are administered in a stimulating effective amount. As used herein, the stimulating effective amount of cells expressing cancer-related antigen refers to the amount that can prolong the in-vivo persistence of the previously administered therapeutic T cells (enhance immune memory) and/or prolong the overall survival period of the subject and/or prolong the recurrence-free survival of the subject after administration. In some embodiments of various aspects of the present invention, the stimulating effective amount of the cells expressing the cancer-related antigen is about $10^3$ to about $10^6$ cells, for example, about $10^3$, about $10^4$, about $10^5$, or about $10^6$ cells. Preferably, a low dose of the cells expressing the cancer-related antigen is administered, for example, about $10^4$ cells. In some embodiments, the dose of cells expressing cancer-related antigen is determined according to the body weight of the subject, and is about $10^3$ to about $10^6$ cells/kg body weight, for example, about $10^3$, about $10^4$, about $10^5$, or about $10^6$ cells/kg body weight. In some embodiments, the dose of cells expressing cancer-related antigens is determined according to the amount of therapeutic T cells administered. For example, the ratio of the amount of therapeutic T cells administered to the amount of cells expressing cancer-related antigen is any ratio between about 1:1 and about 1000:1 or a higher ratio, such as about 1:1, about 2:1, about 3:1, about 4:1, about 5:1, about 6:1, about 7:1, about 8:1, about 9:1, about 10:1, about 50:1, about 100:1 or about 1000:1 or higher.

In some embodiments of the various aspects of the present invention, by administering living cells expressing cancer-related antigen to stimulate existing in-vivo therapeutic T cells (such as CAR-T cells), the persistence of therapeutic T cells in vivo can be increased by at least about 5%, at least about 10%, at least about 20%, at least about 30%, at least about 40%, at least about 50%, at least about 60%, at least about 70%, at least about 80%, at least about 90%, At least about 100%, at least about 150%, at least about 200%, at least about 300% or higher. In some embodiments of the various aspects of the present invention, by administering living cells expressing cancer-related antigen to stimulate existing in-vivo therapeutic T cells (such as CAR-T cells), the overall survival period of the subject can be prolonged by at least about 5%, at least about 10%, at least about 20%, at least about 30%, at least about 40%, at least about 50%, at least about 60%, at least about 70%, at least about 80%, at least about 90%, at least about 100%, at least about 150%, at least about 200%, at least about 300% or higher. In some embodiments of the various aspects of the present invention, by administering living cells expressing cancer-related antigen to stimulate existing in-vivo therapeutic T cells (such as CAR-T cells), the recurrence-free survival period of the subject after remission can be prolonged by at least about 5%, at least about 10%, at least about 20%, at least about 30%, at least about 40%, at least about 50%, at least about 60%, at least about 70%, at least about 80%, at least about 90%, at least about 100%, at least about 150%, at least about 200%, at least about 300% or higher.

In some embodiments of the various aspects of the present invention, the therapeutic T cells are T cells (TCR-T cells) including an exogenous T cell receptor (TCR). In some embodiments, the exogenous TCR (usually includes a α and a β chain) specifically binds to a cancer-related antigen.

In some embodiments of the various aspects of the present invention, the therapeutic T cells are T cells including a chimeric antigen receptor (CAR) (CAR-T cells). A variety of CAR-T cells have been developed in the art, such as first-generation to fourth-generation CAR-T cells, CAR-T cells modified to remove inhibitory signals, etc., all of which can be applied to the present invention.

In some embodiments of various aspects of the invention, the CAR includes an extracellular antigen binding domain against the cancer-related antigen. The extracellular antigen binding domain may be, for example, a monoclonal antibody, a synthetic antibody, a human antibody, a humanized antibody, a single domain antibody, an antibody single-chain variable fragment (scFV), and an antigen-binding fragment thereof. In some preferred embodiments, the extracellular antigen binding domain is scFV. For example, the extracellular antigen binding domain may be derived from one or more known antibodies including any commercially available antibody, such as FMC63, rituximab, alemtuzumab, epratuzumab, trastuzumab, bivatuzumab, cetuximab, labetuzumab, palivizumab, sevirumab, tuvirumab, basiliximab, daclizumab, infliximab, omalizumab, efalizumab, Keliximab, siplizumab, natalizumab, clenoliximab, pemtumomab, Edrecolomab, Cantuzumab, and the like.

In some embodiments of various aspects of the present invention, the CAR further includes a transmembrane domain and an intracellular signal transduction domain. The intracellular signal transduction domain of the CAR according to the present invention is responsible for the intracellular signal transduction after the extracellular ligand binding domain binds to the target, leading to the activation of immune cells and immune response. The intracellular signal transduction domain has the capability to activate at least one normal effector function of immune cells expressing the CAR. For example, the effector function of T cells may be cytolytic activity or auxiliary activity, including the secretion of cytokines.

The intracellular signal transduction domain of a CAR may be a cytoplasmic sequence, such as but not limited to the cytoplasmic sequence of T cell receptors and co-receptors (which act in concert to initiate signal transduction after antigen receptor binding), and any derivative or variant of these sequences and any synthetic sequence with the same functional capability. The Intracellular signal transduction domain includes two different types of cytoplasmic signal transduction sequences: the sequences that initiate antigen-dependent primary activation, and the sequences that act in an antigen-independent manner to provide secondary or co-stimulatory signals. The primary cytoplasmic signal transduction sequence may include a signal transduction motif referred to as the immunoreceptor tyrosine activation motif, ITAM. Non-limiting examples of the ITAM used in the present invention may include those derived from TCRζ, FcRγ, FcRβ, FcRε, CD3γ, CD3δ, CD3δ, CD5, CD22, CD79a, CD79b, and CD66d. In some embodiments, the intracellular signal transduction domain of the CAR may include the CD3δ signal transduction domain. In some embodiments, the intracellular signal transduction domain of the CAR of the present invention further includes a costimulatory domain. In some embodiments, the costimulatory domain is selected from the 41BB costimulatory domain or the CD28 costimulatory domain.

CAR is expressed on the surface of cells. Therefore, the CAR may include a transmembrane domain. The suitable transmembrane domain of the CAR of the present invention has the following capabilities: (a) expression on the cell surface, preferably immune cells, such as but not limited to lymphocytes or natural killer (NK) cells, and (b) interacting with the ligand binding domain and intracellular signal transduction domain to guide the cellular response of immune cells to predetermined target cells. The transmembrane domain may be derived from natural or synthetic sources. The transmembrane domain may be derived from any membrane-binding protein or transmembrane protein. As a non-limiting example, the transmembrane domain may be derived from subunits of T cell receptors such as a subunits, β subunits, γ or δ subunits, polypeptides constituting the CD3 complex, and p55 (α chain), p75 (β chain) or γ of IL-2 receptors, a subunit chain of Fc receptors, especially Fcγ receptor III or CD protein. Alternatively, the transmembrane domain may be synthetic, and may mainly include hydrophobic residues such as leucine and valine. In some embodiments, the transmembrane domain is derived from a human CD8 α chain. The transmembrane domain may further include a hinge region located between the extracellular ligand binding domain and the transmembrane domain. The hinge region is, for example, derived from the extracellular region of CD8, CD4 or CD28. In some embodiments, the hinge region is part of a human CD8α chain.

In some specific embodiments of various aspects of the present invention, the CAR used in the present invention may include an extracellular antigen binding domain that specifically binds cancer-related antigens, a CD8a hinge and a transmembrane domain, a CD3ζ signal transduction domain, and a 4-1BB costimulatory domain.

In a specific implementation manner, the CAR (for CD19) of the present invention includes the following amino acid sequence of SEQ ID NO:1:

(SEQ ID NO: 1)
MALPVTALLLPLALLLHAARPDIQMTQTTSSLSASLGDRVTISCRASQD

ISKYLNWYQQKPDGTVKLLIYHTSRLHSGVPSRFSGSGSGTDYSLTISN

LEQEDIATYFCQQGNTLPYTFGGGTKLEITGGGGSGGGGSGGGGSEVKL

QESGPGLVAPSQSLSVTCTVSGVSLPDYGVSWIRQPPRKGLEWLGVIWG

SETTYYNSALKSRLTIIKDNSKSQVFLKMNSLQTDDTAIYYCAKHYYYG

GSYAMDYWGQGTSVTVSSTTTPAPRPPTPAPTIASQPLSLRPEACRPAA

GGAVHTRGLDFACDIYIWAPLAGTCGVLLLSLVITLYCKRGRKKLLYIF

KQPFMRPVQTTQEEDGCSCRFPEEEEGGCELRVKFSRSADAPAYQQGQN

QLYNELNLGRREEYDVLDKRRGRDPEMGGKPRRKNPQEGLYNELQKDKM

AEAYSEIGMKGERRRGKGHDGLYQGLSTATKDTYDALHMQALPPR.

In a specific implementation manner, the CAR (for CD19) of the present invention is encoded by the following nucleotide sequence of SEQ ID NO: 2:

(SEQ ID NO: 2)
ATGGCCTTACCAGTGACCGCCTTGCTCCTGCCGCTGGCCTTGCTGCTCC

ACGCCGCCAGGCCGGACATCCAGATGACACAGACTACATCCTCCCTGTC

TGCCTCTCTGGGAGACAGAGTCACCATCAGTTGCAGGGCAAGTCAGGAC

ATTAGTAAATATTTAAATTGGTATCAGCAGAAACCAGATGGAACTGTTA

AACTCCTGATCTACCATACATCAAGATTACACTCAGGAGTCCCATCAAG

GTTCAGTGGCAGTGGGTCTGGAACAGATTATTCTCTCACCATTAGCAAC

CTGGAGCAAGAAGATATTGCCACTTACTTTTGCCAACAGGGTAATACGC

TTCCGTACACGTTCGGAGGGGGGACCAAGCTGGAGATCACAGGTGGCGG

TGGCTCGGGCGGTGGTGGGTCGGGTGGCGGCGGATCTGAGGTGAAACTG

CAGGAGTCAGGACCTGGCCTGGTGGCGCCCTCACAGAGCCTGTCCGTCA

CATGCACTGTCTCAGGGGTCTCATTACCCGACTATGGTGTAAGCTGGAT

TCGCCAGCCTCCACGAAAGGGTCTGGAGTGGCTGGGAGTAATATGGGGT

AGTGAAACCACATACTATAATTCAGCTCTCAAATCCAGACTGACCATCA

TCAAGGACAACTCCAAGAGCCAAGTTTTCTTAAAAATGAACAGTCTGCA

AACTGATGACACAGCCATTTACTACTGTGCCAAACATTATTACTACGGT

GGTAGCTATGCTATGGACTACTGGGGCCAAGGAACCTCAGTCACCGTCT

CCTCAACCACGACGCCAGCGCCGCGACCACCAACACCGGCGCCCACCAT

CGCGTCGCAGCCCCTGTCCCTGCGCCCAGAGGCGTGCCGGCCAGCGGCG

-continued

```
GGGGGCGCAGTGCACACGAGGGGGCTGGACTTCGCCTGTGATATCTACA

TCTGGGCGCCCTTGGCCGGGACTTGTGGGGTCCTTCTCCTGTCACTGGT

TATCACCCTTTACTGCAAACGGGGCAGAAAGAAACTCCTGTATATATTC

AAACAACCATTTATGAGACCAGTACAAACTACTCAAGAGGAAGATGGCT

GTAGCTGCCGATTTCCAGAAGAAGAAGAAGGAGGATGTGAACTGAGAGT

GAAGTTCAGCAGGAGCGCAGACGCCCCCGCGTACCAGCAGGGCCAGAAC

CAGCTCTATAACGAGCTCAATCTAGGACGAAGAGAGGAGTACGATGTTT

TGGACAAGAGACGTGGCCGGGACCCTGAGATGGGGGAAAGCCGAGAAG

GAAGAACCCTCAGGAAGGCCTGTACAATGAACTGCAGAAAGATAAGATG

GCGGAGGCCTACAGTGAGATTGGGATGAAAGGCGAGCGCCGGAGGGGCA

AGGGGCACGATGGCCTTTACCAGGGTCTCAGTACAGCCACCAAGGACAC

CTACGACGCCCTTCACATGCAGGCCCTGCCCCCTCGC.
```

In some embodiments of various aspects of the present invention, the cells expressing the cancer-related antigen are living cells. In some embodiments, the cancer-related antigen is expressed on the surface of the living cells. In some embodiments, the cell expressing the cancer-related antigen is not a cancer cell. In some embodiments, the cell expressing the cancer-related antigen is a cell genetically engineered to express the antigen. The type of the cell is not particularly limited, and the cell may be derived from an isolated primary cell, or derived from a cell line. In some embodiments, the cells expressing the cancer-related antigen are derived from peripheral blood cells such as peripheral blood mononuclear cells (PBMCs). In some embodiments, the cells expressing the cancer-related antigen are derived from immune cells, such as macrophages, dendritic cells, plasma cells, granulocytes, mast cells, lymphocytes (inflammatory T lymphocytes, cytotoxic T lymphocytes, regulatory T lymphocytes, or helper T lymphocytes, B lymphocytes), and the like. In some embodiments, the cells may be derived from CD34+ cells. In some embodiments, the cells may be derived from T lymphocytes such as CD4+T lymphocytes or CD8+T lymphocytes. In some embodiments, the cells may be derived from B lymphocytes.

In some embodiments of various aspects of the present invention, the therapeutic T cells and/or the cells expressing cancer-related antigen are derived from autologous cells of the subject. As used herein, "autologous" refers to that cells, cell lines, or cell populations used to treat the subject are derived from the subject. In some embodiments, the therapeutic T cells and/or the cells expressing cancer-related antigen are derived from allogeneic cells, such as from a donor compatible with the subject's human leukocyte antigen (HLA). Standard schemes can be used to convert cells from a donor into non-alloreactive cells and to replicate the cells as required, generating cells that can be administered to one or more patients.

The therapeutic T cells and/or cells expressing cancer-related antigen of the present invention can be prepared by various methods known in the art. For example, expression constructs containing CAR or TCR coding sequences can be used to transduce T cells to obtain CAR-T cells or TCR-T cells. For example, an expression construct containing the coding sequence of a cancer-related antigen can be used to transduce cells to obtain cells expressing the cancer-related antigen. Those skilled in the art can easily construct expression constructs suitable for protein expression.

The cells of the present invention can be obtained from many non-limiting sources by various non-limiting methods, including peripheral blood mononuclear cells, bone marrow, lymph node tissues, umbilical cord blood, thymus tissues, ascites, pleural effusions, spleen tissues and tumors. In some embodiments, cell lines available and known to those skilled in the art can be used. In some embodiments, the cells may be derived from a healthy donor or from a patient diagnosed with cancer. In some embodiments, the cells may be part of a mixed population of cells exhibiting different phenotypic characteristics.

The cells of the present invention, such as T cells, may be activated and proliferated before or after genetic modification. T cells may be proliferated in vitro or in vivo. Generally, the T cells of the present invention may be proliferated, for example, by contacting an agent that stimulates the CD3 TCR complex and costimulatory molecules on the surface of the T cell to generate a T cell activation signal. For example, chemicals such as a calcium ionophore A23187, phorbol 12-myristate 13-acetate (PMA), or mitotic lectins such as phytohemagglutinin (PHA) can be used to generate T cell activation signals. In some embodiments, the T cell population may be activated by contacting in vitro, for example, an anti-CD3 antibody or a antigen-binding fragment thereof, or an anti-CD2 antibody immobilized on a surface, or by contacting a protein kinase C activator (for example, a moss inhibitor) together with the calcium ionophore carrier. For example, under conditions suitable for stimulating T cell proliferation, the T cell population may be in contact with anti-CD3 antibodies and anti-CD28 antibodies. Conditions suitable for T cell culture include suitable culture media that may contain factors necessary for proliferation and viability (such as Minimal Essential Media or RPMI Media 1640, or X-vivo 5, (Lonza)), where the necessary factors include serum (such as fetal bovine or human serum), interleukin-2 (IL-2), insulin, IFN-γ, IL-4, IL-7, GM-CSF, IL-10, IL-2, IL-15, TGFβ and TNF, or additives for cell growth known to those skilled in the art. Other additives for cell growth include but are not limited to surfactants, human plasma protein powder, and reducing agents such as N-acetyl-cysteine and 2-mercaptoacetic acid. The culture media may include RPMI 1640, A1M-V. DMEM, MEM, a-MEM, F-12, X-Vivo 1 and X-Vivo 20, Optimizer, amino acids, sodium pyruvate and vitamins, serum-free or supplemented with appropriate amount of serum (or plasma) or a specific set of hormones, and/or a certain quantity of cytokines sufficient for the growth and proliferation of T cells. The target cells can be maintained under conditions necessary to support growth, such as an appropriate temperature (e.g., 37° C.) and environment (e.g., air plus 5% $CO_2$). T cells exposed to different stimulation times may show different characteristics.

"Subject" used herein refers to an organism suffering from or susceptible to a disease or symptom that can be treated by the method, combination or pharmaceutical composition of the present invention. Non-limiting examples include humans, cattle, rats, mice, dogs, monkeys, goats, sheep, cows, deer, and other non-mammals. In a preferred embodiment, the subject is a human.

In a second aspect, the present invention provides a method for preventing cancer progression or recurrence in a subject, where the subject has undergone treatment (cancer treatment) using therapeutic T cells specifically targeting a cancer-related antigen, the method including administering cells expressing the cancer-related antigen to the subject. The therapeutic T cells or cells expressing cancer-related antigen are as defined herein.

In some embodiments, the cells expressing the cancer-related antigen are administered for one or more times, preferably once.

In some embodiments, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, or about 21 days after the therapeutic T cells are administered, the cells expressing the cancer-related antigen are administered.

In some embodiments, after the therapeutic T cells reduce the cancer cell load, the cells expressing the cancer-associated antigen are administered. For example, after the cancer cell load is reduced by at least about 5%, at least about 10%, at least about 20%, at least about 30%, at least about 40%, at least about 50%, at least about 60%, at least about 70%, at least about 80%, or at least about 90%, cells expressing the cancer-related antigen are administered. In some embodiments, after the cancer is completely remitted by administering the therapeutic T cells, the cells expressing the cancer-associated antigen are administered.

In some embodiments, after the therapeutic T cells are administered, when the amount of the therapeutic T cells in the subject decreases, the cells expressing the cancer-related antigen are administered. The amount of the therapeutic T cells in the subject can be detected by methods such as flow cytometry or quantitative PCR. For example, if the therapeutic T cells are CAR-T cells, the copy number of the CAR-encoding gene in the sample from the subject can be detected by PCR. When the copy number of the CAR-encoding gene decreases, cells expressing the cancer-related antigen are administered.

Therefore, in some embodiments, the method further includes the step of monitoring the tumor load and/or the amount of the therapeutic T cells in the subject after the therapeutic T cells are administered.

In some embodiments, cells expressing cancer-related antigen are administered in a stimulating effective amount. As used herein, the stimulating effective quantity of cells expressing cancer-related antigen refers to the amount that can prolong the in-vivo persistence of the previously administered therapeutic T cells (enhance immune memory) and/or prolong the overall survival period of the subject and/or prolong the recurrence-free survival of the subject after administration. In some embodiments, the stimulating effective amount of the cells expressing the cancer-related antigen is about $10^3$ to about $10^6$ cells, for example, about $10^3$, about $10^4$, about $10^5$, or about $10^6$ cells. Preferably, a low dose of the cells expressing the cancer-related antigen is administered, for example, about $10^4$ cells. In some embodiments, the dose of cells expressing cancer-related antigen is determined according to the body weight of the subject, and is about $10^3$ to about $10^6$ cells/kg body weight, for example, about $10^3$, about $10^4$, about $10^5$, or about $10^6$ cells/kg body weight. In some embodiments, the dose of cells expressing cancer-associated antigen is determined according to the amount of therapeutic T cells previously received by the patient. For example, the ratio of the amount of therapeutic T cells administered to the amount of cells expressing cancer-related antigen is any ratio between about 1:1 and about 1000:1 or a higher ratio, such as about 1:1, about 2:1, about 3:1, about 4:1, about 5:1, about 6:1, about 7:1, about 8:1, about 9:1, about 10:1, about 50:1, about 100:1 or about 1000:1 or higher.

In a third aspect, the present invention provides a combination for treating cancer in a subject, which includes therapeutic T cells specifically targeting a cancer-related antigen and cells expressing the cancer-related antigen. In some embodiments, the combination is used to treat cancer in a subject through the method in the first aspect of the present invention. In some embodiments, the combination includes a therapeutically effective amount of the therapeutic T cells and a stimulating effective amount of the cells expressing the cancer-related antigen. The therapeutic T cells or cells expressing cancer-related antigen are as defined herein.

In a fourth aspect, the present invention provides the use of the combination of the third aspect of the present invention in the preparation of a medicament for treating cancer in a subject. In some embodiments, the medicament is used to treat cancer in a subject through the method in the first aspect of the present invention.

In a fifth aspect, the present invention provides the use of cells expressing a cancer-related antigen in the preparation of a medicament for treating cancer in a subject. For example, the medicament is used in combination with therapeutic T cells that specifically target the cancer-related antigen, to treat cancer in a subject. In some embodiments, the medicament further includes therapeutic T cells that specifically target the cancer-related antigen. In some embodiments, the cells expressing cancer-related antigen and the therapeutic T cells specifically targeting the cancer-related antigen are present separately in the medicament, for example, are placed separately in different containers. In some embodiments, the medicament is used to treat cancer in a subject by the method of the first aspect of the invention. The therapeutic T cells or cells expressing cancer-related antigen are as defined herein.

In a sixth aspect, the present invention provides the use of cells expressing a cancer-related antigen in preparation of a medicament for preventing cancer progression or recurrence in a subject, where the subject has undergone treatment (cancer treatment) using therapeutic T cells that specifically target the cancer-related antigen. In some embodiments, the medicament includes a stimulating effective amount of the cells expressing the cancer-related antigen. In some embodiments, the medicament is used to prevent cancer progression or recurrence in a subject by the method of the second aspect of the present invention. The therapeutic T cells or cells expressing cancer-related antigen are as defined herein.

In a seventh aspect, the present invention provides the use of therapeutic T cells specifically targeting a cancer-related antigen in preparation of a medicament for treating cancer in a subject, where the medicament further includes cells expressing the cancer-related antigen. In some embodiments, the therapeutic T cells specifically targeting the cancer-related antigen and the cells expressing cancer-related antigen are present separately in the medicament, for example, are placed separately in different containers. In some embodiments, the medicament is used to treat cancer in a subject by the method of the first aspect of the present invention. The therapeutic T cells or cells expressing cancer-related antigen are as defined herein.

In an eighth aspect, the present invention provides cells expressing a cancer-related antigen, which are used in combination with therapeutic T cells specifically targeting the cancer-related antigen to treat cancer in a subject. In some embodiments, the cells expressing cancer-related antigen are used to treat cancer in a subject by the method of the first aspect of the present invention. The therapeutic T cells or cells expressing cancer-related antigen are as defined herein.

In a ninth aspect, the present invention provides cells expressing a cancer-related antigen for use in preventing cancer progression or recurrence in a subject, where the subject has undergone treatment (cancer treatment) with therapeutic T cells specifically targeting the cancer-related antigen. In some embodiments, the cells expressing cancer-related antigen are used to prevent cancer progression or recurrence in a subject by the method of the second aspect of the present invention. The therapeutic T cells or cells expressing cancer-related antigens are as defined herein.

In a tenth aspect, the present invention provides therapeutic T cells specifically targeting cancer-related antigens, which are used in combination with cells expressing the cancer-related antigen to treat cancer in a subject. In some embodiments, the therapeutic T cells specifically targeting cancer-related antigen are used to treat cancer in a subject by the method of the first aspect of the present invention. The therapeutic T cells or cells expressing cancer-related antigen are as defined herein.

In an eleventh aspect, the present invention provides a kit including therapeutic T cells specifically targeting a cancer-related antigen and/or cells expressing the cancer-related antigen, and the kit is used for treating cancer or preventing cancer progression or recurrence in the subject through the method of the present invention. In some embodiments, the cells expressing cancer-related antigen and the therapeutic T cells specifically targeting the cancer-related antigen are present separately in the kit, for example, are placed separately in different containers. The therapeutic T cells or cells expressing cancer-related antigens are as defined herein.

The cells or medicaments of the present invention may also contain "pharmaceutically acceptable excipients" or "pharmaceutically acceptable carriers", which refer to substances that help the active substance to be administered to and absorbed by the subject, and may be included in the pharmaceutical composition of the present invention without causing significant toxic and side effects in patients. Non-limiting examples of pharmaceutically acceptable excipients include water, NaCl, physiological saline, lactated Ringer's, normal sucrose, normal glucose, binders, fillers, disintegrants, lubricants, coatings, sweeteners, flavoring agents, salt solutions (such as Ringer's solution), alcohol, oil, gelatin, carbohydrates such as lactose, amylose or starch, fatty acid esters, hydroxymethyl cellulose, polyvinylpyrrolidone and coloring agents. Such preparation may be sterilized. If desired, it can be combined with auxiliary agents such as lubricants, preservatives, stabilizers, wetting agents, emulsifiers, salts that affect osmotic pressure, buffers, colorants and/or fragrances. These auxiliary agents do not deleteriously react with the cells of the present invention. Those skilled in the art understand that other pharmaceutical excipients can also be used in the present invention.

The cancer-related antigens of the present invention are preferably cancer-specific antigens, including but not limited to CD16, CD64, CD78, CD96, CLL1, CD116, CD117, CD71, CD45, CD71, CD123, CD138, ErbB2 (HER2/neu), carcinoembryonic antigen (CEA), epithelial cell adhesion molecule (EpCAM), epidermal growth factor receptor (EGFR), EGFR variant III (EGFRVIII), CD19, CD20, CD30, CD40, disialylganglioside GD2, ductal epithelial mucin, gp36, TAG-72, glycosphingolipid, glioma-related antigens, β-human chorionic gonadotropin, a-fetoglobulin (AFP), lectin-responsive AFP, thyroglobulin, RAGE-1, MN-CA IX, human telomerase reverse transcriptase, RU1, RU2 (AS), intestinal carboxyl esterase, mut hsp70-2, M-CSF, prostase, prostatase specific antigen (PSA), PAP, NY-ESO-1, LAGA-la, p53, Prostein, PSMA, survival and telomerase, prostate cancer tumor antigen-1 (PCTA-1), MAGE, ELF2M, neutrophil elastase, ephrin B2, CD22, insulin growth factor (IGF1)-I, IGF-II, IGF1 receptor, mesothelin, major histocompatibility complex (MHC) molecules that present tumor-specific peptide epitopes, 5T4, ROR1, Nkp30, NKG2D, tumor stromal antigen, fibronectin extra domain A (EDA) and extra domain B (EDB), tenascin-C A1 domain (TnC A1), fibroblast-associated protein (fap), CD3, CD4, CD8, CD24. CD25, CD33, CD34, CD133, CD138, Foxp3, B7-1 (CD80), B7-2 (CD86), GM-CSF, cytokine receptor, endothelial factor, BCMA (CD269, tumor necrosis factor receptor superfamily member 17 (TNFRSF17), (UniProtKB identifier: Q02223)), SLAM family member 7 (SLAMF7) (UniProtKB identifier: Q9NQ25), G-protein coupled receptor family C group 5 member D (GPRC5D) (UniProtKB identifier: Q9NZD1), Peptidyl-prolyl cis-trans isomerase (FKBP11) (UniProtKB identifier: Q9NYL4), KAMP3, Integrin alpha-8 (ITGA8) (UniProtKB identifier: P53708) and FCRLS (UniProtKB identifier: Q68SN8). In a specific embodiment, the cancer-related antigen is CD19.

Non-limiting examples of the cancer of the present invention include lung cancer, ovarian cancer, colon cancer, rectal cancer, melanoma, kidney cancer, bladder cancer, breast cancer, liver cancer, lymphoma, hematological malignancies, head and neck cancers, glial tumor, stomach cancer, nasopharyngeal cancer, throat cancer, cervical cancer, uterine body tumor and osteosarcoma. Examples of other cancers that can be treated with the method or pharmaceutical composition of the present invention include: bone cancer, pancreatic cancer, skin cancer, prostate cancer, skin or intraocular malignant melanoma, uterine cancer, anal cancer, testicular cancer, fallopian tube cancer, endometrial cancer, vaginal cancer, vaginal cancer, Hodgkin's disease, non-Hodgkin's lymphoma, esophageal cancer, small intestine cancer, endocrine system cancer, thyroid cancer, parathyroid cancer, adrenal cancer, soft tissue sarcoma, urethral cancer, penile cancer, chronic or acute leukemia (including acute myeloid leukemia, chronic myeloid leukemia, acute lymphocytic leukemia, and chronic lymphocytic leukemia), childhood solid tumors, lymphocytic lymphoma, bladder cancer, kidney or ureteral cancer, renal pelvis cancer, central nervous system (CNS) tumor, primary CNS lymphoma, tumor angiogenesis, spinal tumor, brainstem glioma, pituitary adenoma, Kaposi's sarcoma, epidermal carcinoma, squamous cell carcinoma, T cell lymphoma, and environmentally induced cancers, including asbestos-induced cancers, and combinations of the cancers. In a specific embodiment, the cancer is B-cell acute lymphoblastic leukemia (B-ALL).

In various aspects of the present invention, the treatment or prevention method can be combined with one or more therapies against cancer that are selected from the following group: antibody therapy, chemotherapy, cytokine therapy, dendritic cell therapy, gene therapy, hormone therapy, laser therapy and radiation therapy.

The administration of the cells or combinations or medicaments according to the invention can be carried out in any convenient way, including injection, infusion, implantation or transplantation. Administration of the cells or combinations or medicaments described herein may be intravenous, intralymphatic, intradermal, intratumoral, intramedullary, intramuscular, or intraperitoneal administration. In an embodiment, the cells or combinations or medicaments of the present invention are preferably administered by intravenous injection.

EXAMPLES

The following will further illustrate the present invention by way of examples, but the present invention is not limited to the scope of the described examples.

Materials and Methods

Generation of CRISPR/Cas9-Mediated B-NDG Mice

CRISPR/Cas9-mediated B-NDG mice were generated by Beijing Biocytogen Co., Ltd. In short, it involves sgRNA targeting of the target regions flanking the first and last exons of the Il2rg locus. For each target site, the CRISPR design tool (crispr.mit.edu/) was used to determine 4 candidate sgRNAs and the UCA kit (Beijing Biocytogen) was used to screen the target activities. Two types of sgRNA were selected and injected into mouse fertilized eggs. Cas9 mRNA and sgRNA transcribed in vitro were mixed at different concentrations and co-injected into the fertilized eggs of NOD-scid mice. After injection, the surviving fertilized eggs were transferred into the fallopian tubes of KM pseudopregnant females. From the F0 primary modified mice, Il2rg-deficient heterozygous and homozygous mice (B-NDG mice) were further generated. All mice were kept in a specific pathogen-free facility.

Cell Lines

293-T cells (ATCC, CRL-3216) were cultured in DMEM (Hyclone, Logan, Utah, USA) supplemented with 10% FBS and 100 U/ml penicillin/streptomycin. Raji (ATCC, CCL-86), Raji-Fluc, (Academy of Military Medical Sciences, Beijing; Derived From Raji Cells by Transfection of Lentiviral Vectors Encoding Fluorescein and Puromycin Resistance), CD19-K562 and K562 cells (Genomeditech, Shanghai) were cultured in RPMI 1640 supplemented with 10% FBS and 100 U/ml penicillin/streptomycin. Irradiated Raji-Fluc cells were obtained by exposing cells to 40Gy cobalt radiation. All culture media and antibiotics were purchased from Gibco Life Technologies (Carlsbad, CA, USA).

Construction, Preparation and Titration of Lentivirus-Based Vectors

The anti-CD19 CAR includes the scFv of CD19-specific FMC63 mAb, the hinge and transmembrane region of CD8, the 4-1BB costimulatory domain and the intracellular CD3ζ chain of the TCR complex. The anti-CD19 CAR gene was cloned into the lentiviral vector pPVLV2 (Pharosvaccine Inc., Gyeonggi, Republic of Korea). The vector was used to generate CAR-T-19 cells.

aT19 lentiviral expression construct was generated by substituting CD19 coding sequence with anti-CD19 CAR coding sequence. The vector was used to generate aT19 cells.

The lentivirus expressing the anti-CD19 CAR or CD19 was produced as follows: 293T cells grown in DMEM containing 10% FBS were co-transfected with lentiviral vector plasmids and pMDLg/pRRE, pRSV-Rev and pMD.G packaging plasmids using PEI (Polysciences Inc., Warrington, PA, USA) transfection reagent. After transfection for 24 hours, the culture medium was replaced with DMEM supplemented with 2% FBS, 1 mM sodium pyruvate and 2 mM L-glutamine. 24 hours after the culture medium exchange, the virus supernatant was collected, concentrated by ultrafiltration and titrated with 293T cells. To determine the functional transduction unit/mL, 293T cells were transduced with serially diluted concentrated lentiviral preparations. After 72 hours, cells were collected and analyzed by flow cytometry.

Generation of CAR-T-19 Cells and aT19 Cells

Fresh peripheral blood mononuclear cells (PBMC) were obtained from blood collected from healthy volunteers. The PBMC was immediately used in a culture medium containing 90% human AB serum plus 10% dimethyl sulfoxide or frozen in the culture medium for future use. PBMC was stimulated with paramagnetic beads (Invitrogen, Carlsbad, CA, USA) coated with anti-CD3 and anti-CD28 monoclonal antibodies at a ratio of 3:1 for 24 hours. After T cell activation, the cells were resuspended in the IMSF100 culture medium at $1 \times 10^6$/mL and mixed with the lentiviral vector in the presence of 8 µg/ml polybrene (SIGMA, St. Louis, MO, USA). The multiplicity of infection (MOI) is 0.5 to 2 and transferred to a 12-well plate. The plate was centrifuged by using a horizontal rotor centrifuge at 1200 g for 2 hours at ambient temperature, then was transferred to a 37° C., 5% $CO_2$ incubator. After 24 hours of incubation, the transduced cells were collected and washed with IMSF100 culture medium, and then the cells were incubated in a culture medium supplemented with 500 IU/mL IL-2 (BMI, Korea). After that, the culture medium and IL-2 (300 IU/mL) were changed every 2 or 3 days, and the culture was maintained at 37° C./5% $CO_2$ until injected into mice. CAR-T-19 cells are T cells expressing the anti-CD19 CAR. aT19 cells are T cells that express CD19.

Flow Cytometry

In order to detect T, B and NK cells and CAR-T cells in mice, multicolor flow cytometry analysis was performed using Becton Dickinson (BD) fluorescence activated cell sorting (FACS) standards according to the manufacturer's protocol. Peripheral blood was collected from the right ventricle. Splenocytes were collected and filtered through a BD cell strainer. Red blood cells and spleen cells in the blood were depleted by the lysis solution. Leukocytes were detected by single or double staining with antibodies including PerCP-CD3, FITC-CD4, PE-CD8, FITC-CD19 and APC-CD49. All antibodies were purchased from Biolegend.

Immunophenotyping analysis was performed by flow cytometry. The efficacy of CAR gene transduction was monitored by staining cells with the following specific antibodies: CD45 (PerCP-Vio770), CD3 (FITC), CD4 (Vio Green), CD16 (APC), CD56 (APC), CD19 (APC-Vio770), and CD14 (Vio Blue; Miltenyi Biotec, Bergisch Gladbach, Germany). The transduced T cells were labeled with biotin-SP (long spacer) AffiniPure F(ab') fragment goat anti-mouse IgG, F(ab')2 fragment specific (Jackson ImmunoResearch Lab), and then labeled with streptavidin-PE (BD Biosciences) or CARTEST-19 (CytoCares Inc., Shanghai, China), and then detected by a CytoFLEX flow cytometer. CytExpert (2.0) software was used to analyze data.

Leukocytes and spleen cells harvested from mice were stained with FITC-CD45, PE-CAR, FITC-CD19 and APC-CD45RO (BD, NJ) and checked in the FACSCanto II flow cytometer (BD). Spleen cells were collected and filtered through the BD cell strainer. The red blood cells were depleted in the blood and spleen cell preparations by incubating for 5 minutes in the lysis solution (BD).

Animal Experiments

The mice in this study were raised and operated according to the guidelines established by the Laboratory Animal Care Evaluation and Identification Association. The study was approved by the NIFDC Institutional Animal Care and Use Committee. Four-week-old female BALB/c, C57BL/6, NOD-scid and B-NDG mice were obtained from the NIFDC Institute of Laboratory Animal Resources (Beijing, China). On D0, mice were implanted with $5 \times 10^5$ Raji-Fluc cells via tail vein injection, and then $2 \times 10^7$ CAR-T-19 cells were implanted on day 5 (D5) or day 6 (D6). In the CAR-T memory experiment, different doses of Raji-Fluc cells, radiated Raji-Fluc cells or aT19 cells were injected on D10 or D11. The bioluminescence signals of all mice were observed at the specified time point. Blood samples are obtained at specified time points for fluorescence-activated cell sorting and quantitative real-time PCR (qPCR) analysis.

Bioluminescence Imaging Analysis

In short, the IVIS-Lumina II imaging system (PerkinElmer, Baltimore, MD) was used to obtain bioluminescence imaging of mice. The mice were anesthetized by intraperitoneal injection of sodium pentobarbital (75 mg/kg body weight). Then 10 minutes later, the mice received intraperitoneal injection of D-luciferin (75 mg/kg body weight; PE). The images were analyzed using Living Image software (Caliper Life Sciences) and the data was expressed as total flux (photons/s). If the maximum bioluminescence value generated exceeds $1 \times 10^6$ flux, and the bioluminescence area is no longer less than $1 \times 10^6$ flux at a subsequent time point, this time point is recorded as the time when the tumor recurs.

Cytotoxicity of CAR-T-19 Cells

The capability of CAR-T-19 cells to kill K562, CD19-K562, aT19 and Raji-Fluc cells was measured by flow cytometry. In short, the target cells (K562, CD19-K562, Raji-Fluc or aT19) were transferred to a centrifuge tube and stained with CFSE. Next, the ratio of target cells to CAR-T-19 cells was adjusted and cells were inoculated in different ratios (K562 or CD19-K562: CAR-T-19=1:1, 1:3 or 1:6; aT19 or Raji-Fluc: CAR-T-19=1:0.3, 1:1 or 1:3). Untransduced T cells were recorded as NC (negative control). After incubation for 20-24 hours, the percentage of CFSE+7-AAD+ cells was analyzed by flow cytometry.

Quantitative Detection of CAR-T Cells

The presence of CAR genes in CAR-T-19 cells separated from peripheral blood and spleens of mice was detected through qPCR. In short, DNA was extracted using the QIAamp® DNA Mini Kit (Qiagen, GER) and quantified in the IMPLEN N50 ultra-micro ultraviolet spectrophotometer (IMPLEN, N80 TOUCH). The extracted DNA was stored at −20° C. until needed. PCR amplification of DNA (100 ng) was performed using the 4-1BB primer (Invitrogen) and probe (Thermo Fisher Scientific), to detect the expression of CAR genes the CD19 4-1BB F primer, 5'-TGCCGATTTCCAGAAGAAGAAGAAG-3' (SEQ ID NO: 3); the CD19 4-1BB R primer, 5'-GCGCTCCTGCTGAACTTC-3' (SEQ ID NO:4); the CD19 4-1BB MGB probe, and 5'-ACTCTCAGTTCACATCCTC-3' (SEQ ID NO:5).

PCR was performed by using a StepOnePlus fluorescent real-time quantitative PCR instrument (Thermo Fisher). The results were analyzed using Step One Software v2.3.

Statistics

All charts were generated using GraphPad® Prism 6.0 software. All statistical comparisons were performed through non-parametric one-way analysis of variance or Student t tests. P value<0.05 is statistically significant (*), P<0.01 (**) is very significant.

Example 1. Generation and Characterization of Raji-B-NDG Mouse Model

Non-obese diabetic severe combined immunodeficiency (NOD-scid) mice with invalid Il2rg lack mature T cells, B cells and natural killer (NK) cells, and lack cytokine signaling, leading to better implantation of multiple cancer types. In this embodiment, CRISPR/Cas9 genome editing technology was used to delete the Il2rg gene from NOD-scid mice to prepare B-NDG mice (FIG. 1A). It was observed that the B-NDG mice were viable, reproducible and did not show any obvious physical abnormality. Compared with NOD-scid mice, FACS analysis showed that the spleen and peripheral blood of B-NDG mice had lower numbers of CD19+B cells, CD4+ and CD8+ T cells (FIG. 1B). NOD-scid mice had a high percentage of CD49b+NK cells (spleen 20.90%, peripheral blood 24.10%), while B-NDG mice had no functional NK cells (spleen 1.45%, peripheral blood 5.95%). Therefore, B-NDG mice generated through genome editing were phenotypically similar to NSG mice.

The rapidly growing non-Hodgkin lymphoma cell line Raji cells were genetically engineered to stably express the firefly luciferase reporter gene for bioluminescence imaging (Raji-Fluc). CD19 luminescence abundance on the Raji-Fluc cell surface was detected by flow cytometry. The results showed that CD19 was highly expressed on Raji-Fluc cells (FIG. 1G). After the corresponding substrate of Fluc was added in vitro, the luminous intensity of Fluc was positively correlated with the number of Raji-Fluc cells ($R^2=0.99$, FIG. 1G).

In order to further study the capabilities of the obtained B-NDG mouse model, five different mouse strains (including CB57/L mice as normal controls, nude mice and rag2−/− mice as part of the immunodeficiency group, NOD-scid and B-NDG mice) at the 6-week-old age were transplanted with Raji-Fluc cells through tail vein injection. The bioluminescence signal was detected on the fourth day (D4) after implantation (PI) in B-NDG mice, and it increased by 1000 times after 16 days (FIG. 1C and FIG. 1D). Flow cytometry analysis showed that CD19+ Raji cells burst in the peripheral blood of B-NDG mice, and the correlation with the bioluminescence signal was $R^2=0.90$ (FIG. 1E). However, Raji-Fluc cells could not be detected in CB57/L, rag2−/−, nude mice, and even NOD-scid mice. All four types of mice survived on D30 after PI, while 7 B-NDG mice died on D18 after PI, and the other 3 died on D19 (FIG. 1C, FIG. 1D, and FIG. 1F). The data proves that Raji cell implantation in B-NDG mice has a much better effect and can be used as a model for testing therapeutic agents such as CAR-T cells.

Example 2. In-Vitro and In-Vivo Efficiencies of CD19 Targeting CAR-T Cells

Figure 2:
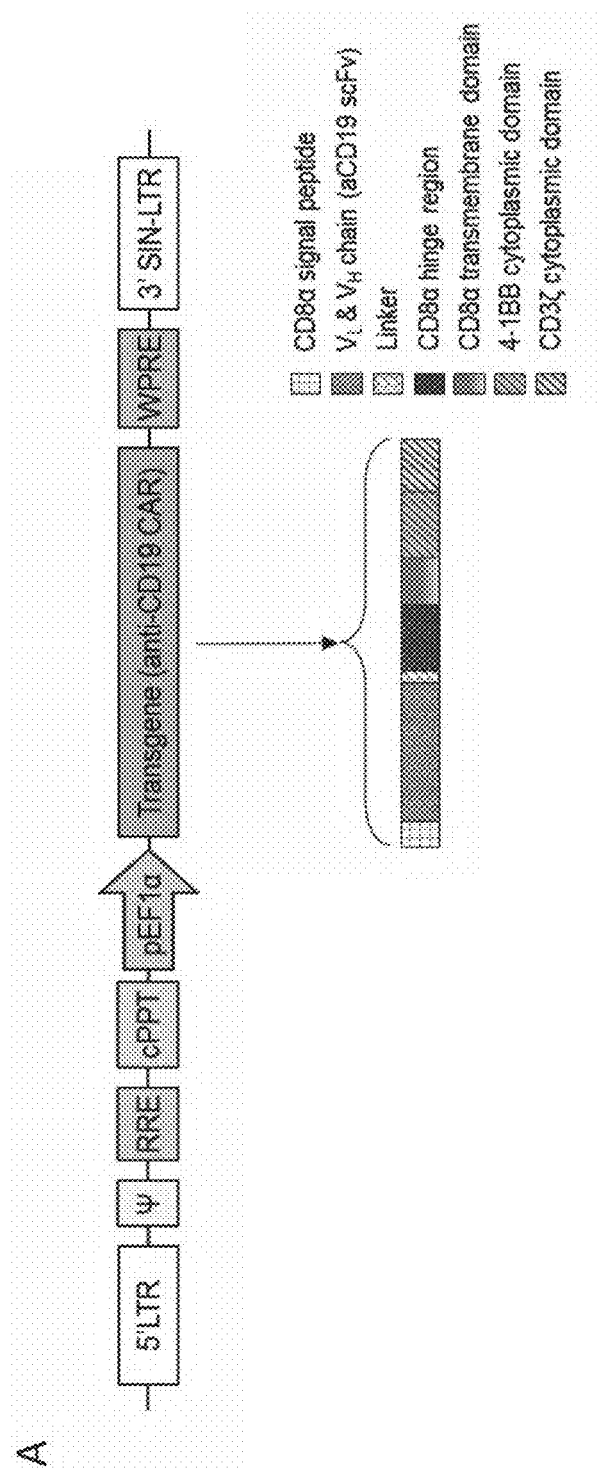
FIG. 2. In-vitro CD19 CAR-T cell efficiency. (A) The structure of anti-CD19 CAR. (B) Summary of in-vitro culture of CAR-T cells from PBMC donors, including the percentage of living cells, the total cell count of CAR-T cells, and the percentage of CAR-T cells. (C) The cytotoxic effect of CAR-T cells on in-vitro Raji cells when the CAR-T/Raji ratio is 1:1, 3:1 and 6:1.
Figure 2:
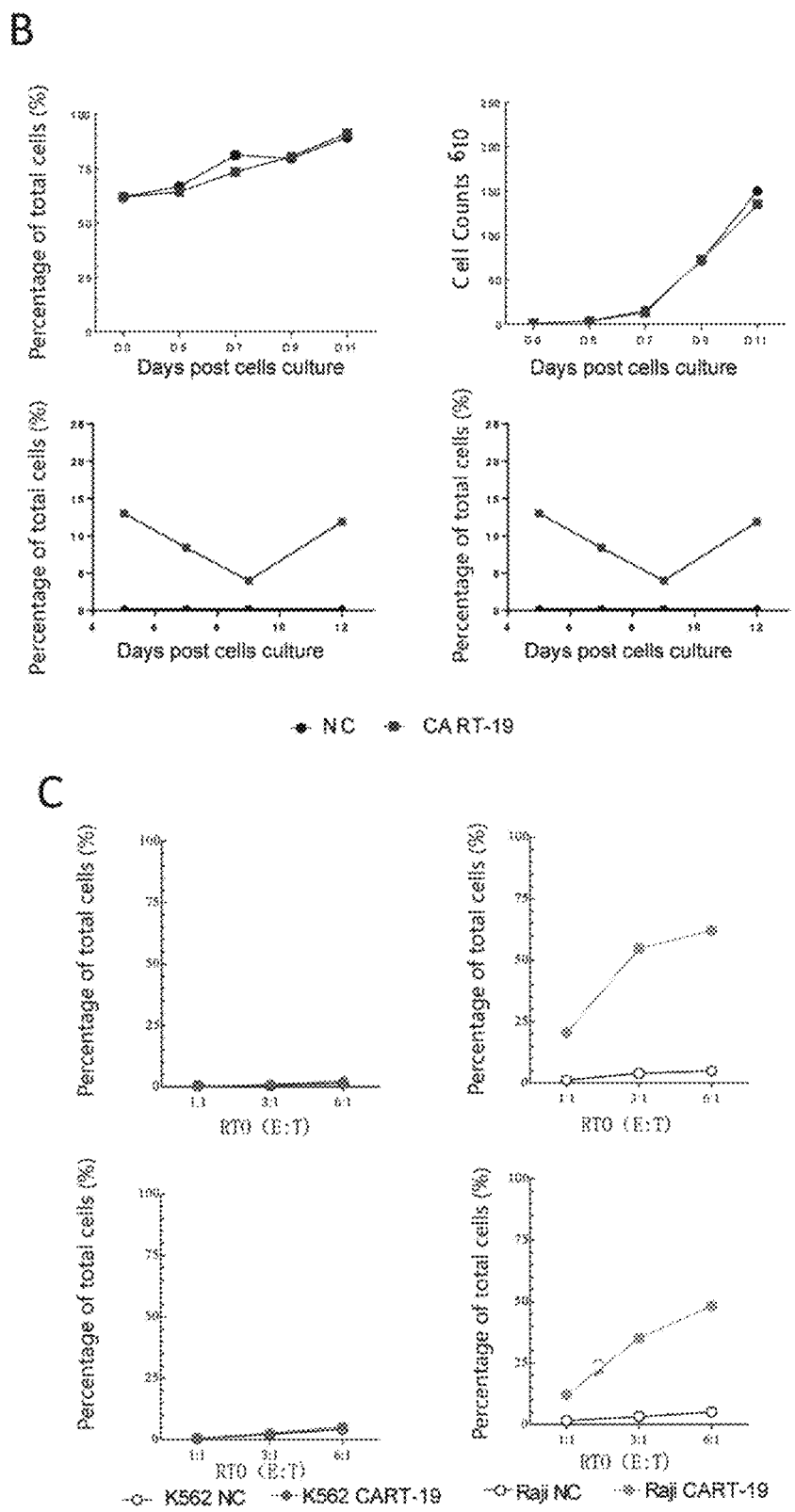

After T cell activation, PBMC separated from volunteers were transduced with the second-generation CAR (FIG. 2A). The results showed that the proportion of CD19 CAR-T cells increased with the extension of culture time, reaching 20% on D12, and the total number of cells on D10 after infection was greater than $1 \times 10^8$ (FIG. 2B). When co-cultured with CD19+ Raji cells in vitro, CD19 CAR-T cells cultured for 12 days showed more than 50% killing effect on Raji cells when the ratio of effector cells/target cells is about 3:1. In order to further verify the anti-tumor effect of CD19 CAR-T cells in vivo, B-NDG mice were injected with $5 \times 10^5$ Raji-Fluc cells through the tail vein, and then implanted with $2 \times 10^7$ CD19 CAR-T cells 5 days later. After CD19 CAR-T treatment for four days (D9), the bioluminescence signals of these treated mice were close to those of mice without tumors (FIG. 3A), indicating that CD19 CAR-T cells successfully mediated tumor clearance in vivo.

Example 3. Source of Recurrence of Raji Tumor

Figure 3:
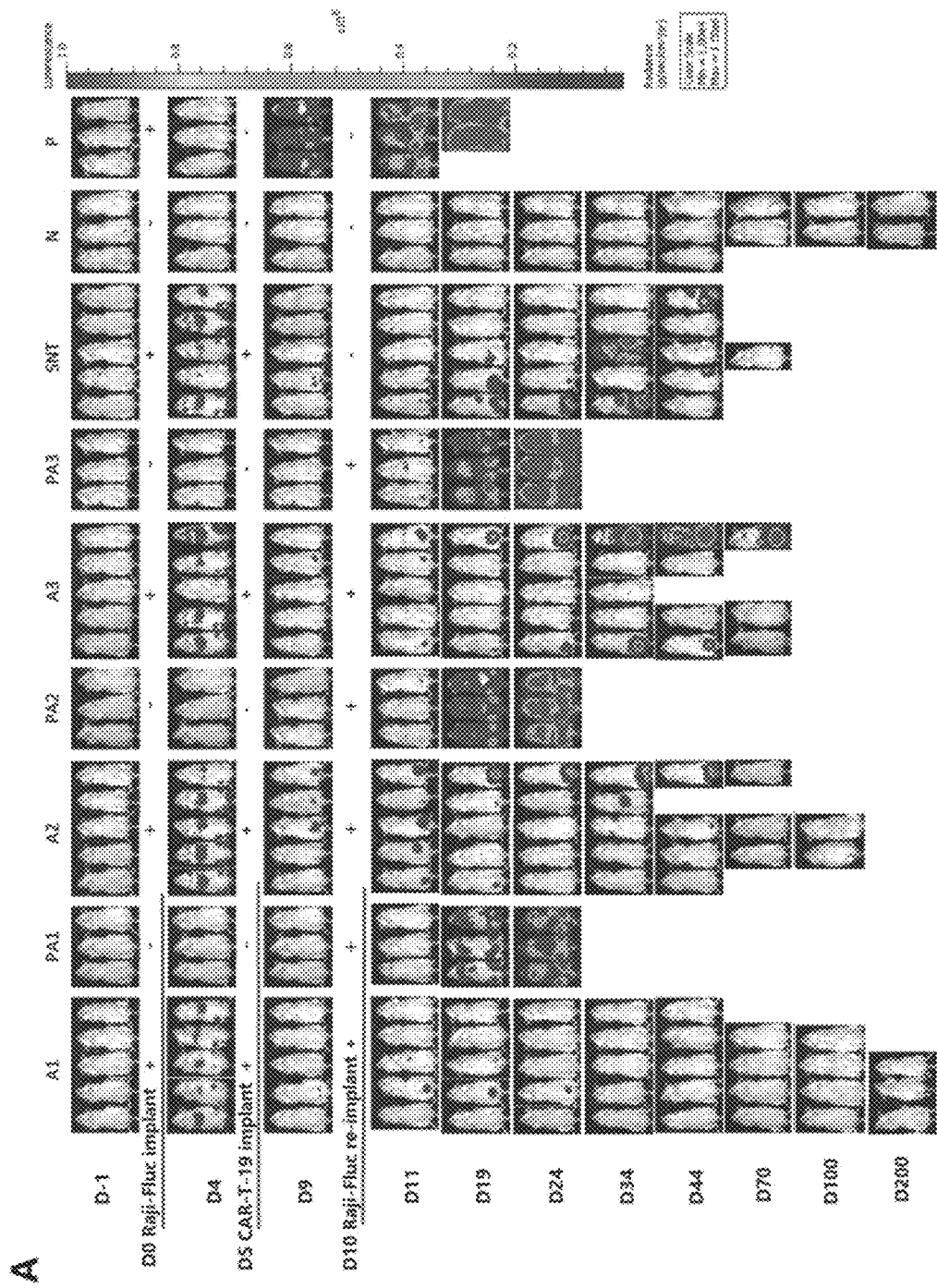
FIG. 3. Re-stimulation of low-dose live tumor cells promoted the generation of immune memory of CAR-T cells. (A) Separate measurement of the fluxes of organs and tissues in different groups. (B) Reimplantation of low-dose live tumor cells can promote tumor clearance and prolong overall survival. (C) Reimplantation of low-dose live tumor cells can delay recurrence. (D) The average total flux of each group. LT: low-dose reimplantation; MT: medium-dose reimplantation; HT: high-dose reimplantation.
Figure 3:
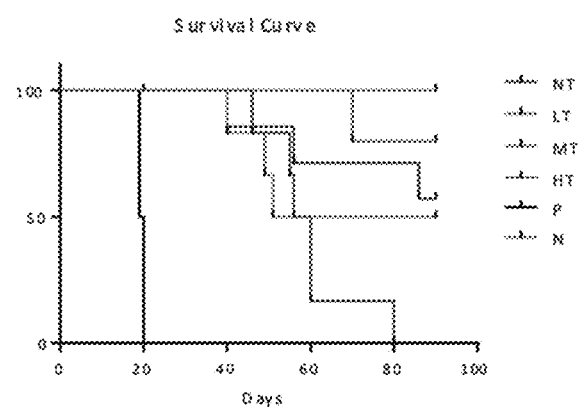
Figure 3:
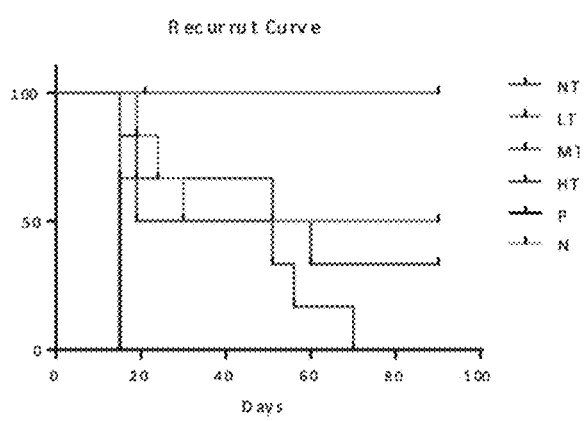
Figure 3:
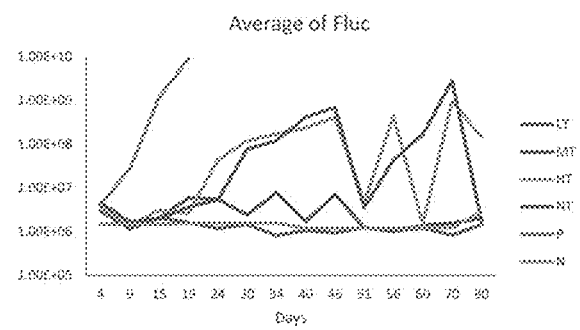

Although CAR-T cells were effective, B-NDG mice eventually die from tumors. In order to find the source of Raji cell recurrence, the bioluminescence of all major organs in mice was tested. The results showed that Raji cells were significantly cleared by CD19 CAR-T cells in the spleen, heart and skin. For example, in the spleen, the bioluminescence was reduced by 1000 times after treatment with CAR-T cells (FIG. 3A). However, CD19 CAR-T is not so effective in all other organs, especially in the liver and brain (FIG. 3A). Residual Raji cells that hide in these organs and that cannot be effectively cleared by CAR-T may be the cause of tumor recurrence.

Example 4. Stimulation of Low-Dose Live Tumor Cells Helps the Generation of Immune Memory of CAR-T Cells In order to test whether CAR-T cells changed due to the tumor microenvironment, causing the CAT-T cells to fail to recognize and kill Raji cells and leading to disease recurrence, in the case that bioluminescence was not detected on D10 after PI, different quantities of Raji-Fluc cells were reimplanted into CD19 CAR-T-treated mice (A1: $5 \times 10^4$, A2: $5 \times 10^5$, A3: $5 \times 10^6$). Mice that were not re-vaccinated with Raji-Fluc cells were used as controls (SNT). In the SNT group, bioluminescence could be observed continuously until all mice died. After another day of implantation, all mice developed diseases rapidly. Unexpectedly, after reimplantation for 9 days, almost all Raji cells were cleared (FIG. 3A). The survival of the reimplantation group was better than that of the SNT group (P<0.05, FIG. 3A and FIG. 3B). Three mice in group A1 survived for more than 200 days. If the maximum bioluminescence value of a mouse exceeds $1 \times 10^6$ flux at a certain time point, and the bioluminescence area is no longer less than $1 \times 10^6$ flux at a subsequent time point, the time point is recorded as the tumor recurrence time. Compared with other groups, re-inoculation with low-dose Raji-Fluc cells can prolong the recurrence-free time (FIG. 3A and FIG. 3C). Then the average bioluminescence intensity of different groups at different time points is analyzed. The signal of the low-dose reimplantation group was close to that of the blank control group (FIG. 3D), while the signals of the other groups increased to varying degrees, indicating that the recurrence was caused by the poor persistence of CAR and its insufficient capability, and the low-dose tumor cell antigen stimulation promoted the generation of CAR-T cell immune memory.

Example 5. Reimplantation of Tumor Cells Killed by Radiation Did not Work

Figure 4:
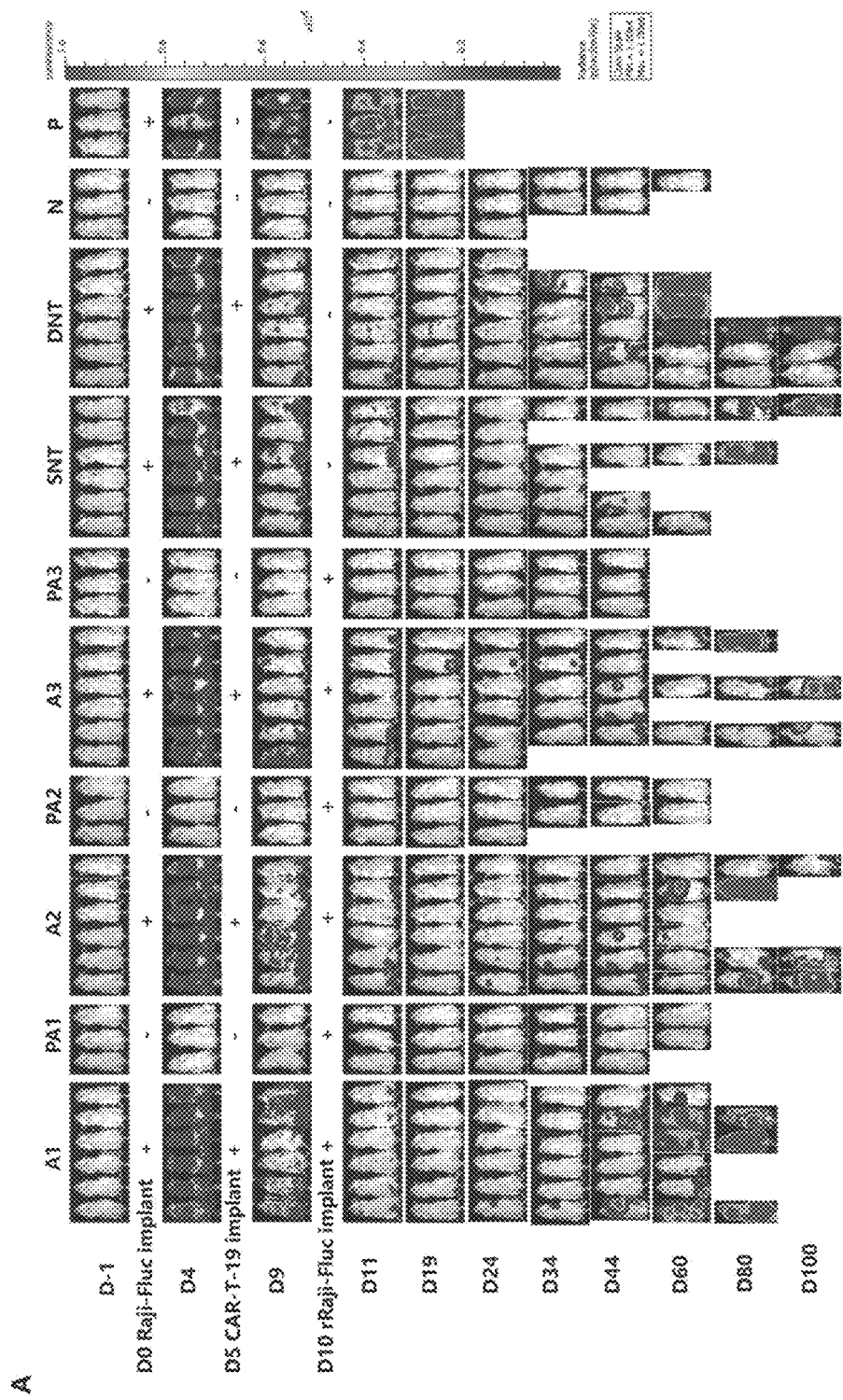
FIG. 4. Reimplantation of tumor cells killed by radiation did not work. (A) Separate measurement of the fluxes of organs and tissues in different groups. (B) and (C) Reimplantation of tumor cells killed by radiation cannot prolong overall survival and recurrence-free survival. The effect of dual treatment of CAR-T cells is the same as that of single treatment. (D) Measurement of the number of CAR-T cells in peripheral blood of mice through qPCR.
Figure 4:
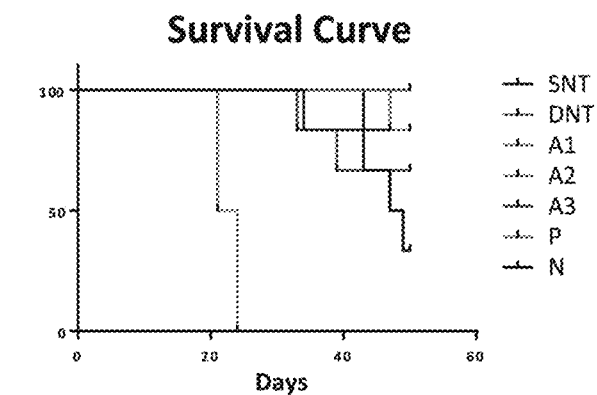
Figure 4:
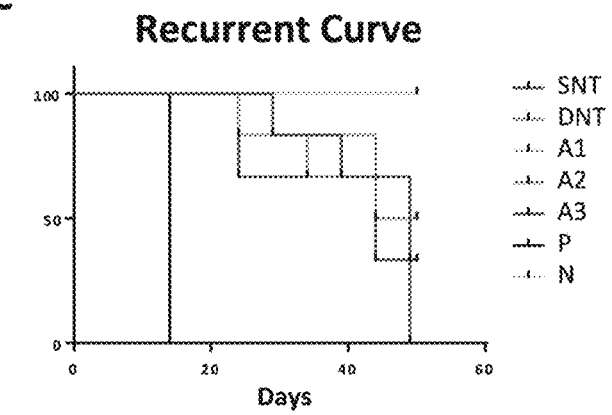
Figure 4:
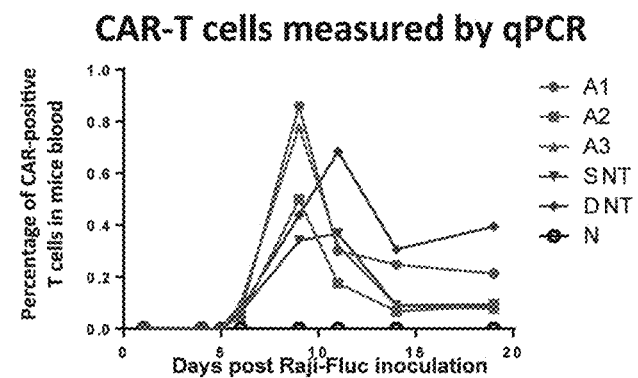

It is not feasible to inject live tumor cells clinically, and therefore, it is tested whether tumor cells that die after radiation can stimulate the immune memory of CAR-T cells. Since multiple infusions of CAR-T cells are currently the main strategy to overcome the lack of persistence in the field, a mouse model of repeated CAR-T treatment has been designed. As shown in FIG. 4, after CAR-T cell treatment on day 5 (D5), Raji-B-NDG mice were injected with different doses of radiated Raji-Fluc cells (rRaji-Fluc, A1: $5 \times 10^4$. A2: $5 \times 10^5$, A3: $5 \times 10^6$) on D10. Three groups of B-NDG mice inoculated with the same dose of rRaji-Fluc are used as the radiated cell control group (PA1/PA2/PA3). Mice without rRaji-FLuc implantation served as single treatment group (SNT). Mice in the dual treatment group (DNT) were injected with $2 \times 10^7$ CAR-T cells on D10. Bioluminescence signals could be observed in mice until all mice in the SNT group died. Compared with the SNT group, reimplantation of rRaji-Fluc cells could not prolong the overall survival period and recurrence-free survival period of the mice (FIG. 4B and FIG. 4C). There was no significant difference between the SNT group and the DNT group, indicating that the dual treatment is ineffective. The number of CAR-T cells in the peripheral blood of mice in the A1/A2/A3/SNT group reached a peak at a similar time (FIG. 4D). Due to two injections of CAR-T cells, the peak time of the DNT group was later than that of other groups. The reduction rate of CAR-T cells in the A1 group was slower than that in the A2/A3/SNT group, indicating that the stimulation of low-dose rRaji-Fluc cells tended to promote the maintenance of CAR-T cells.

Example 6. Re-Stimulation Using T Cells Expressing CD19 (aT19)

Figure 5:
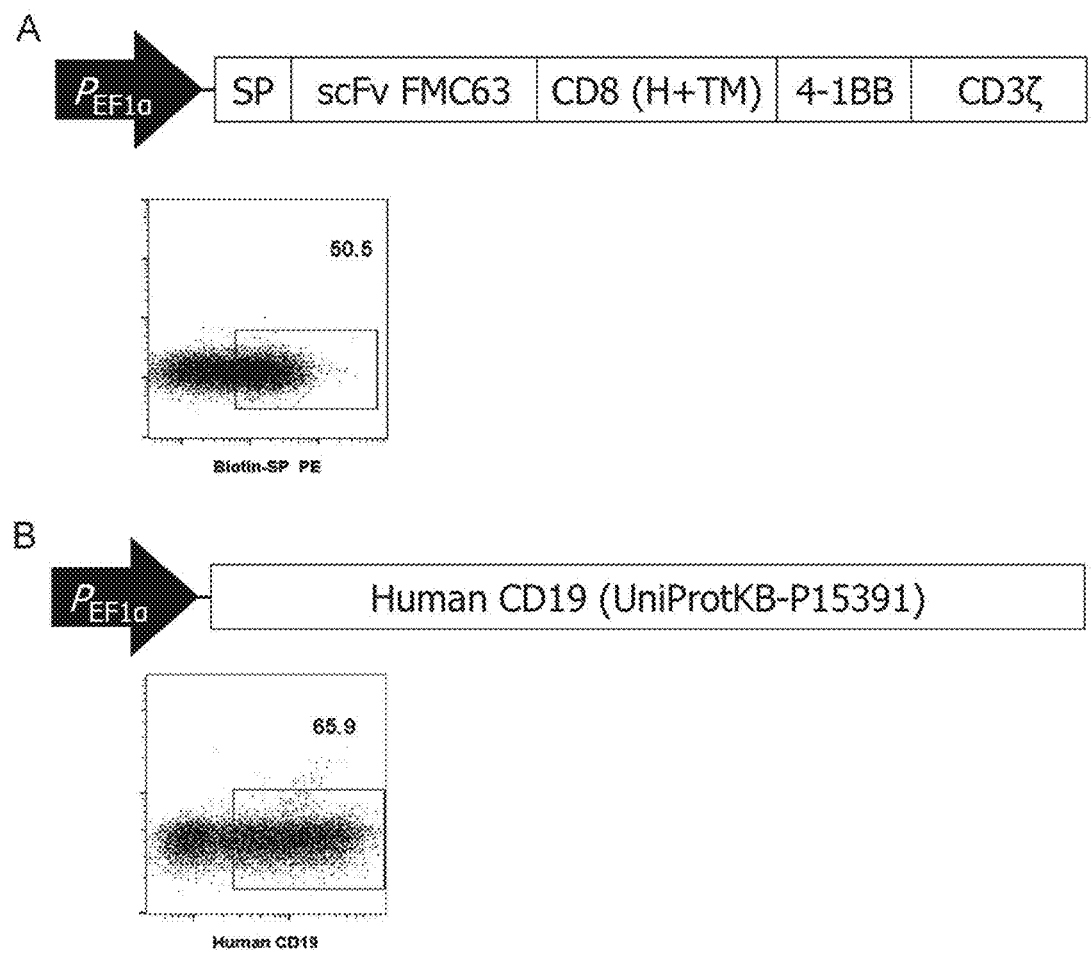
FIG. 5. Characterization of CAR-T-19 and aT19 cells. (A) Schematic diagram showing the structure of the CAR-19 gene construct and the CAR-T-19 transduction efficiency of primary activated T cells. (B) The structure of the human CD19 gene construct and the CD19 transduction efficiency of primary activated T cells. (C) The cytotoxic effect of CAR-T-19 cells on CD19-K562 or K562 cells when the ratio of CAR-T-19: CD19-K562 or K562 is 1:1, 3:1 and 6:1; and the cytotoxic effect of CAR-T-19 cells on Raji-Fluc or aT19 cells when the CAR-T-19: Raji-Fluc or aT19 ratio is 0.3:1, 1:1, and 3:1.
Figure 5:
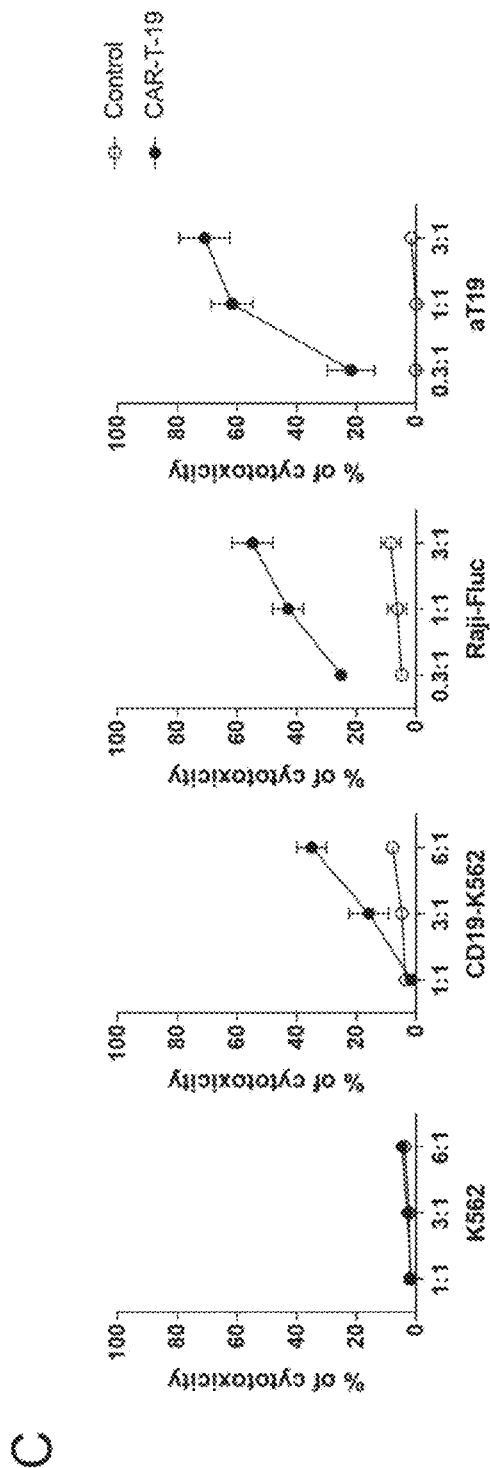

The CAR gene construct contains scFv derived from CD19-specific FMC63 mAb, the hinge and transmembrane region of CD8, and the cytoplasmic domain of 4-1BB, and the intracellular CD35 chain of the TCR complex (FIG. 5A). pEF1α is the CAR gene promoter. The aT19 construct was generated by replacing the CAR transgene with human CD19 (FIG. 5B). T cells separated from PBMC obtained from healthy volunteers were transduced with CAR-19 or CD19 construct (aT19). Table 1 shows the phenotypes and numbers of CAR-T-19, live Raji-Fluc, radiated Raji-Fluc and aT19 cells used in the experiment. Next, a cytotoxicity assay was performed, to check the killing capability of CAR-T-19 cells. After being co-cultured with CD19+ Raji or aT19 cells in vitro, CAR-T-19 cells killed more than 50% of Raji-Fluc cells or aT19 with an effector/target ratio greater than 3:1, and when T cells were co-cultured with control K562 cells, almost no cytotoxicity was observed (FIG. 5C).

TABLE 1

The number of live Raji-Fluc, radiated Raji-Fluc and aT19 cells used in the experiment, as well as the phenotype and number of CAR-T-19

| Experiments | CD4+ | CD8+ | CAR+ | Number of CAR-T cells | Restimulation cells Number |
|---|---|---|---|---|---|
| Restimulation of live Raji-Fluc | 63.09% | 32.04% | 50.45% | $2 \times 10^7$ | $5 \times 10^4$ |
| | | | | | $5 \times 10^5$ |
| | | | | | $5 \times 10^6$ |
| Re-stimulation of radiated Raji-Fluc | 42.63% | 53.52% | 62.85% | $2 \times 10^7$ | $5 \times 10^4$ |
| | | | | | $5 \times 10^5$ |
| | | | | | $5 \times 10^6$ |
| Re-stimulation of aT19 | 43.00% | 54.08% | 70.95% | $2 \times 10^7$ | $5 \times 10^5$ |

Figure 6:
FIG. 6. Re-stimulation of CAR-T cells by live Raji tumor cells increased survival rate and delayed tumor recurrence. Raji-Fluc cells are injected intravenously (i.v.) on D0 ($2 \times 10^5$ cells per mouse; groups A1, A2, A3, NT, and P). On D5 after the injection of Raji-Fluc cells, mice received i.v. injection of CAR-T-19 cells ($2 \times 10^7$ cells per mouse; groups A1, 2, 3, and NT). On D10, mice were i.v. injected with Raji-Fluc cells of different doses (groups A1 and PA1: $5 \times 10^4$; groups A2 and PA2: $1.5 \times 10^5$; and groups A3 and PA3: $5 \times 10^5$). The group PA is used as a control for the group A. (A) Schematic diagram showing the timetable of animal experiments. (B) Bioluminescence image showing the total fluxes in the organs and tissues of different groups of mice. Kaplan-Meier survival curves are constructed based on different doses of reimplanted Raji-Fluc cells to monitor the eradication of systemic diseases (C) and estimate recurrence-free survival (D).
Figure 6:
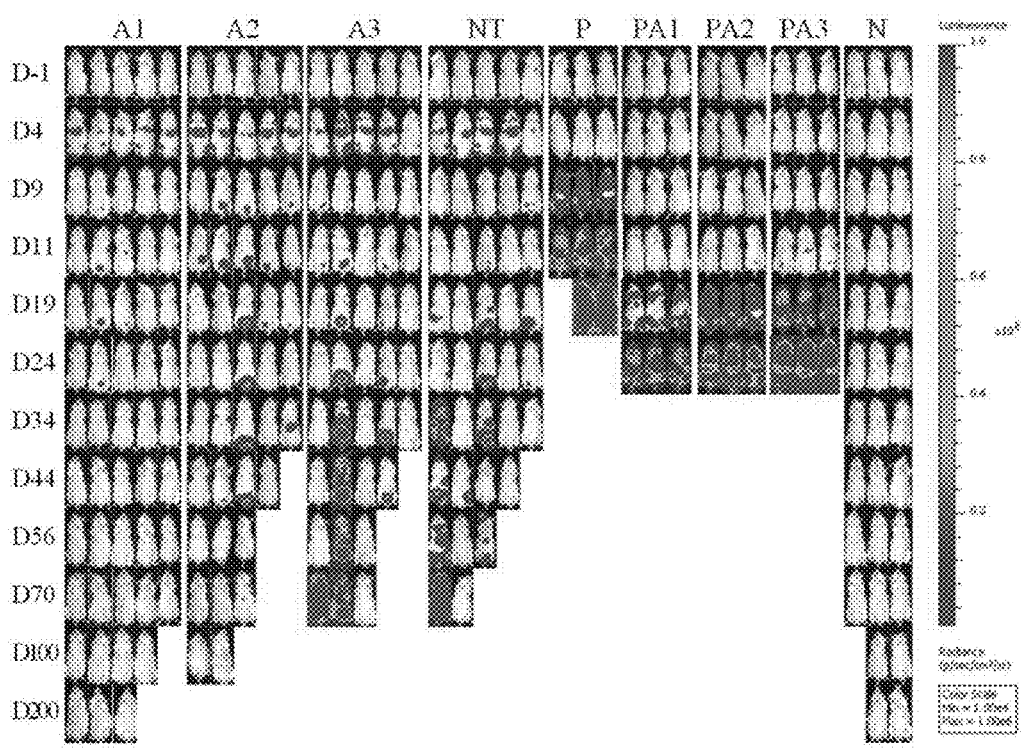
Figure 6:
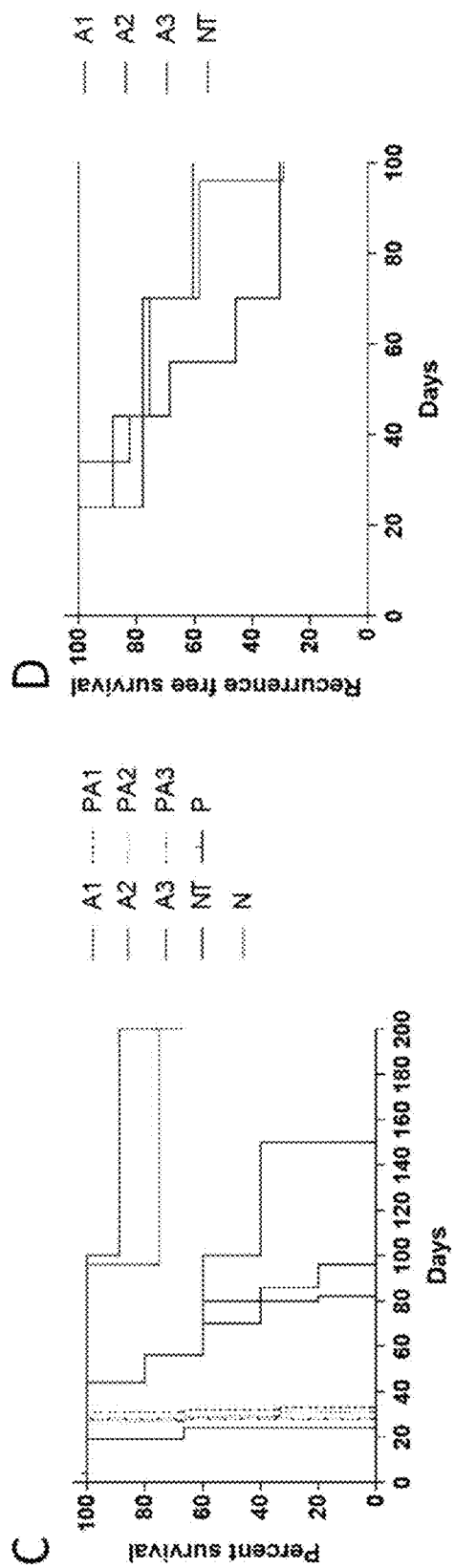

CAR-T-19 Treatment Followed by Administration of Live Raji-Fluc Cells can Prolong the Survival of Raji-B-NDG Mice Mice in the positive group and NC group received tumor cells separately or received only PBS, and were respectively recorded as group P or group N (n=3/group). Mice in the NT group received CAR-T-19 cells without stimulation (n=5/group). Group A was designated as the immune memory test group. The mice in this group received one of three different doses of restimulation cells (group A1, $5 \times 10^4$ cells; group A2, $1.5 \times 10^5$ cells; and group A3, $5 \times 10^5$ cells) (n=5/group). Groups PA1, 2, and 3 were separately used as the control group of each group A (n=3/group). These groups are listed in Table 2. FIG. 6A shows the use timeline of tumor cells, CAR-T cells and restimulation cells.

TABLE 2

The number of Raji-Fluc cells used in the restimulation experiment

| Time/type of injected cells | A1 (n = 5) | A2 (n = 5) | A3 (n = 5) | P (n = 3) | N (n = 3) | NT (n = 5) | PA1 (n = 3) | PA2 (n = 3) | PA3 (n = 3) |
|---|---|---|---|---|---|---|---|---|---|
| D0/Raji-Fluc | $5 \times 10^5$ | $5 \times 10^5$ | $5 \times 10^5$ | $5 \times 10^5$ | / | $5 \times 10^5$ | / | / | / |
| D5/CAR-T | $2 \times 10^7$ | $2 \times 10^7$ | $2 \times 10^7$ | / | $2 \times 10^7$ | $2 \times 10^7$ | / | / | / |
| D10/Raji-Fluc | $5 \times 10^4$ | $1.5 \times 10^5$ | $5 \times 10^5$ | / | / | / | $5 \times 10^4$ | $1.5 \times 10^5$ | $5 \times 10^5$ |

In-vivo imaging results obtained after injection (PI) on D4 showed that the total flux ($>2.2\times10^6$) of mice receiving Raji-Fluc cells was much higher than that ($<1.6\times10^6$; group NC) of mice not receiving Raji-Fluc cells, indicating that the mouse model was successfully constructed (FIG. 6B). On D5 of PI, mice received (or did not receive) $2\times10^7$ CAR-T-19 cells. The imaging on D9 showed that the total flux of all mice receiving CAR-T-19 cells (except those in group P) was significantly reduced (FIG. 6B), indicating that CAR-T-19 cells effectively killed Raji-Fluc cells.

Next, in order to study whether Raji-Fluc cells stimulate the growth of residual CAR-T-19 cells, generate memory cells, and prolong the effect of CAR-T-19 treatment, mice received subsequent injection of Raji-Fluc cells on D10 of PI. As shown in FIG. 6B, all mice in group P died on D18 to D23 of PI. All mice in the group PA1/2/3 died on D31-33/D27-31/D28 respectively. Since the mice in the group PA3 received the same number of tumor cells as the mice in the group P, the survival time was similar to that on D20 to D24. One mouse in group N died on D71 for unknown reasons. The other two survived for more than 200 days. All 5 mice in the group NT died on D82. For mice in the group A1, the fluorescence signal gradually decreased from D11 to D24, and Raji-Fluc cells were not detected on D34 (FIG. 6B). Three mice in this group were tumor-free on D200. In the group A2, three mice died on D96, while the other two mice survived to D100 without tumors (FIG. 6B). In the group A3, one mouse died for unknown reasons on D40, three died on D56, D80 and D86 due to tumor recurrence, and the other one died on D96. In short, these results indicated that the mice restimulated with tumor cells survived longer than those that were not restimulated tumor cells (FIG. 6C, P<0.05). In addition, re-inoculation with low-dose Raji-Fluc cells resulted in a significant increase in a recurrence-free survival rate (FIG. 6D). Finally, the average bioluminescence intensity of different groups at different time points was checked. The signal generated by the low-dose restimulation group was very similar to the signal generated by the blank control group (FIG. 6B), while the signals produced by the other groups increased to varying degrees, indicating that the low-dose tumor cell restimulation was used to expand the CAR-T-19 cell population and clear Raji-Fluc cells.

Figure 7:
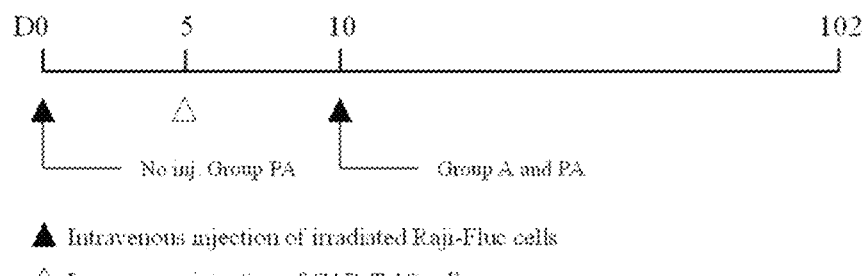
FIG. 7. Re-stimulation of CAR-T cells with tumor cells killed by radiation was ineffective. Raji-Fluc cells were injected intravenously (i.v.) on D0 ($2 \times 10^5$ cells per mouse; groups A1, A2, A3, NT, and P). On D5 after the injection of Raji-Fluc cells, mice received i.v. injection of CAR-T-19 cells ($2 \times 10^7$ cells per mouse; groups A1, A2, A3, and NT). On D10, mice were i.v. injected with Raji-Fluc cells of different doses (groups A1 and PA1: $5 \times 10^4$; groups A2 and PA2: $1.5 \times 10^5$; and groups A3 and PA3: $5 \times 10^5$). The group PA was used as a control for the group A. (A) Schematic diagram showing the timetable of animal experiments. (B) Bioluminescence image showing the total fluxes in the organs and tissues of different groups of mice. Kaplan-Meier survival curves were constructed based on different doses of reimplanted Raji-Fluc cells to monitor the eradication of systemic diseases (C) and estimate recurrence-free survival (D). (E) Quantitative polymerase chain reaction was used to detect CAR+ cells in the blood of group A and group NT after implantation of Raji-Fluc cells. The graph shows the gene copy number of CAR in blood samples from each group.
Figure 7:
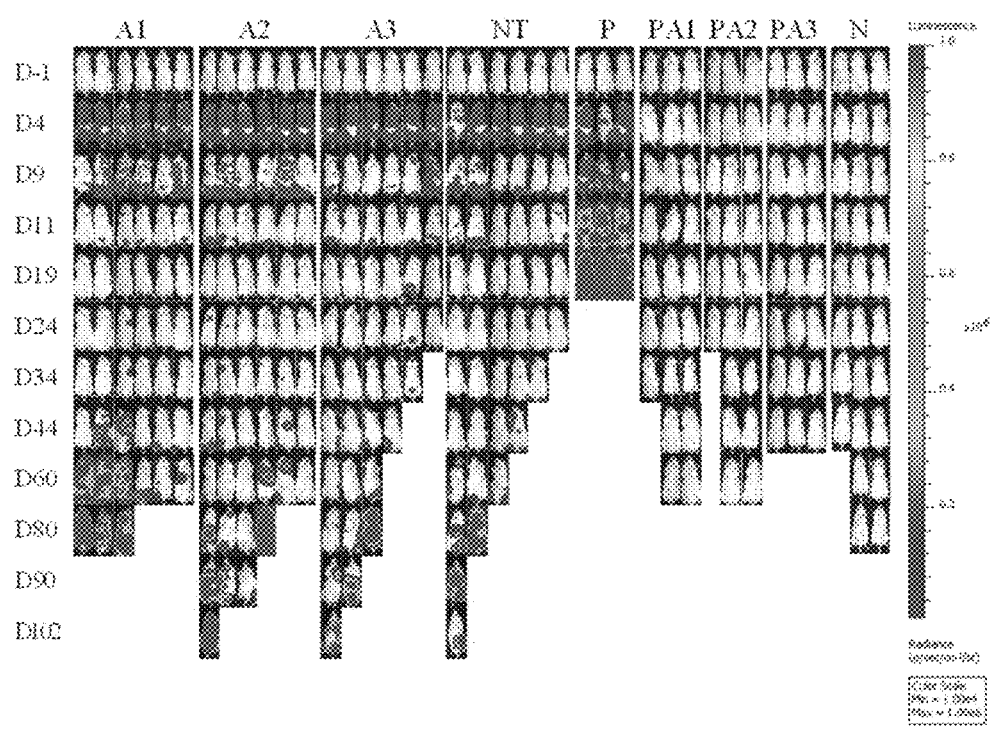
Figure 7:
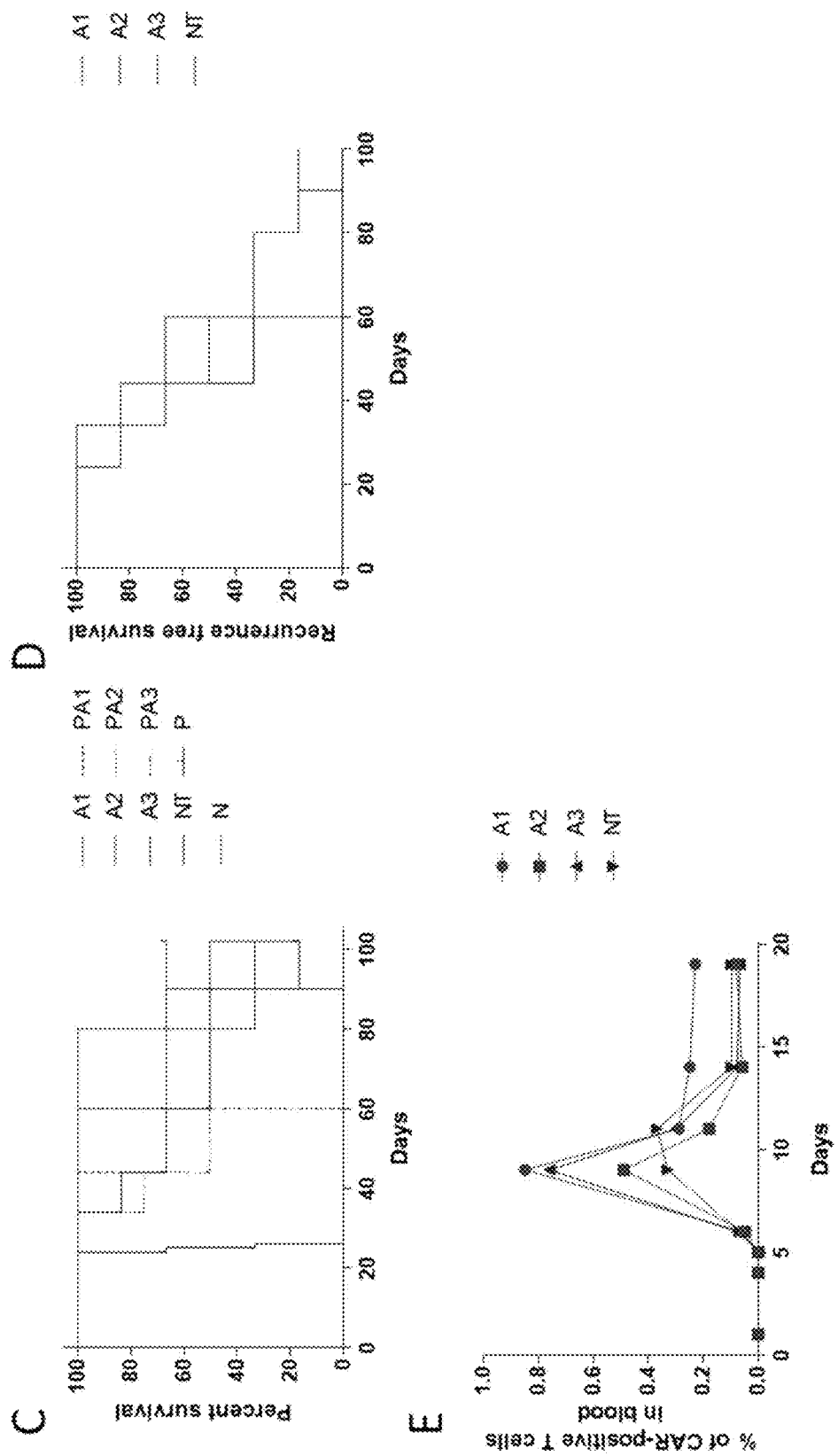

Continuous Treatment of Raji-B-NDG Mice with CAR-T-19 Cells Followed by Radiated Raji-Fluc Cells Did not Prolong the Survival Period It is not feasible to inject live tumor cells into patients. Therefore, the next study is to investigate whether tumor cells that died after radiation increase the efficacy of CAR-T-19 cells in a manner similar to that of living cells. This set of experiments used the same mouse group as the live cell experiment. The groups and numbers of cells administered are shown in Table 3. The timeline is shown in FIG. 7A. As described above, bioluminescence imaging was performed at different times of PI. It was found that restimulation of CAR-T-19 cells with radiated dead Raji-Fluc cells did not increase the overall survival rate and recurrence-free survival rate (FIG. 7B and FIG. 7C).

TABLE 3

Number of radiated Raji-Fluc cells used for restimulation

| Time/type of injected cells | A1 (n = 6) | A2 (n = 6) | A3 (n = 6) | NT (n = 6) | P (n = 3) | N (n = 3) | PA1 (n = 3) | PA2 (n = 3) | PA3 (n = 3) |
|---|---|---|---|---|---|---|---|---|---|
| D0/Raji-Fluc | $5 \times 10^5$ | $5 \times 10^5$ | $5 \times 10^5$ | $5 \times 10^5$ | $5 \times 10^5$ | / | / | / | / |
| D5/CAR-T | $2 \times 10^7$ | $2 \times 10^7$ | $2 \times 10^7$ | $2 \times 10^7$ | / | / | / | / | / |
| D10/radiated Raji-Fluc | $5 \times 10^4$ | $1.5 \times 10^5$ | $5 \times 10^5$ | / | / | / | $5 \times 10^4$ | $5 \times 10^5$ | $5 \times 10^6$ |

In addition, the number of CAR copies (representing the number of CAR+ cells) of blood obtained from the mouse inner canthus was measured on D0/D5/D10/D15/D20. As shown in FIG. 7E, the number of CAR-T-19 cells in the groups A1, A2, A3 and NT reached their peaks at the same time. In addition, after restimulation with radiated tumor cells on D10, the number of CAR copies did not increase (FIG. 7E). These results show that that restimulation of radiated dead tumor cells radiation will not increase the growth of residual CAR-T-19 cells or promote the generation of memory CAR-T-19 cells.

Figure 8:
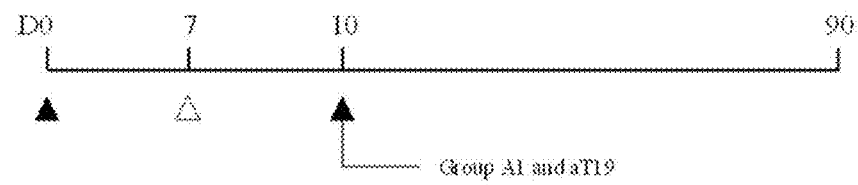
FIG. 8. Continuous treatment with CAR-T-19 and aT19 cells promoted the generation of memory CAR-T cells. Raji-Fluc cells were injected intravenously (i.v.) on D0 ($2 \times 10^5$ cells per mouse; groups A1, NT, aT19, and P). On D7 after the injection of Raji-Fluc cells, mice received i.v. injection of CAR-T-19 cells ($2 \times 10^7$ cells per mouse; groups A1, NT, and aT19). On D10, mice in the group A1 received i.v. injection of $5 \times 10^4$ cells, mice in the group aT19 received i.v. injection of $5 \times 10^5$ cells, and the other groups did not receive injection. (A) Schematic diagram showing the timetable of animal experiments. (B) Bioluminescence image showing the total fluxes in the organs and tissues of different groups of mice. (C) Construction of Kaplan-Meier survival curves to monitor the eradication of systemic diseases. Quantitative polymerase chain reaction was used to detect CAR+ cells in blood (D) and spleen (E) on D10, D20, and D30. The graph shows the gene copy number of CAR in samples from each group. (F) Percentage of CAR+ and CD45RO+ cells in peripheral blood.
Figure 8:
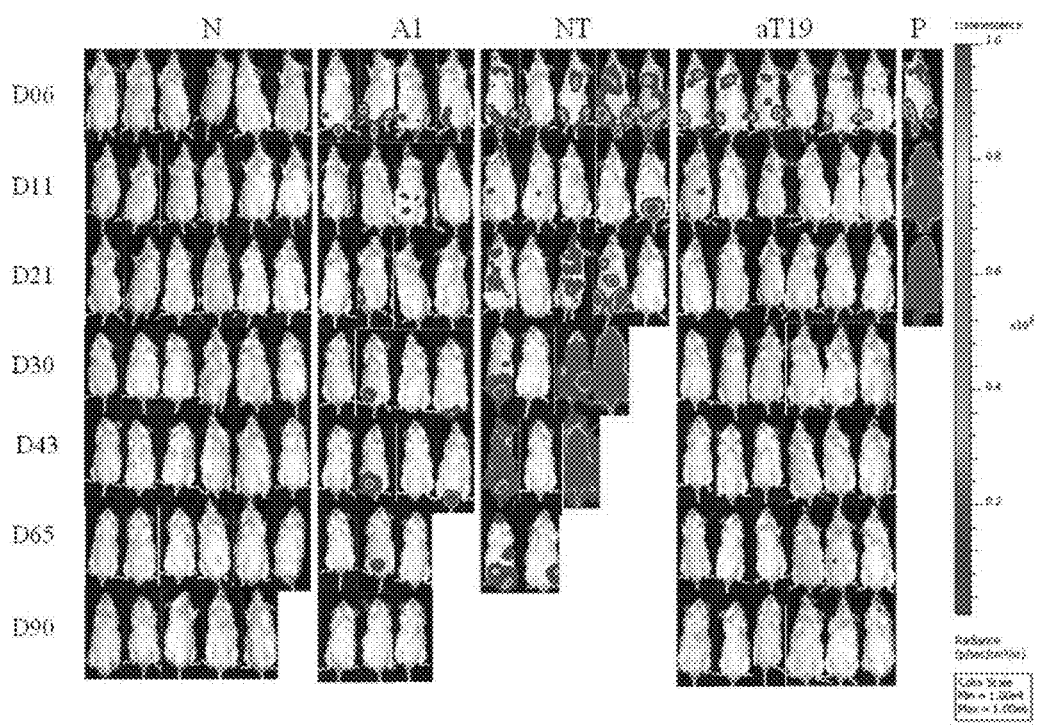
Figure 8:
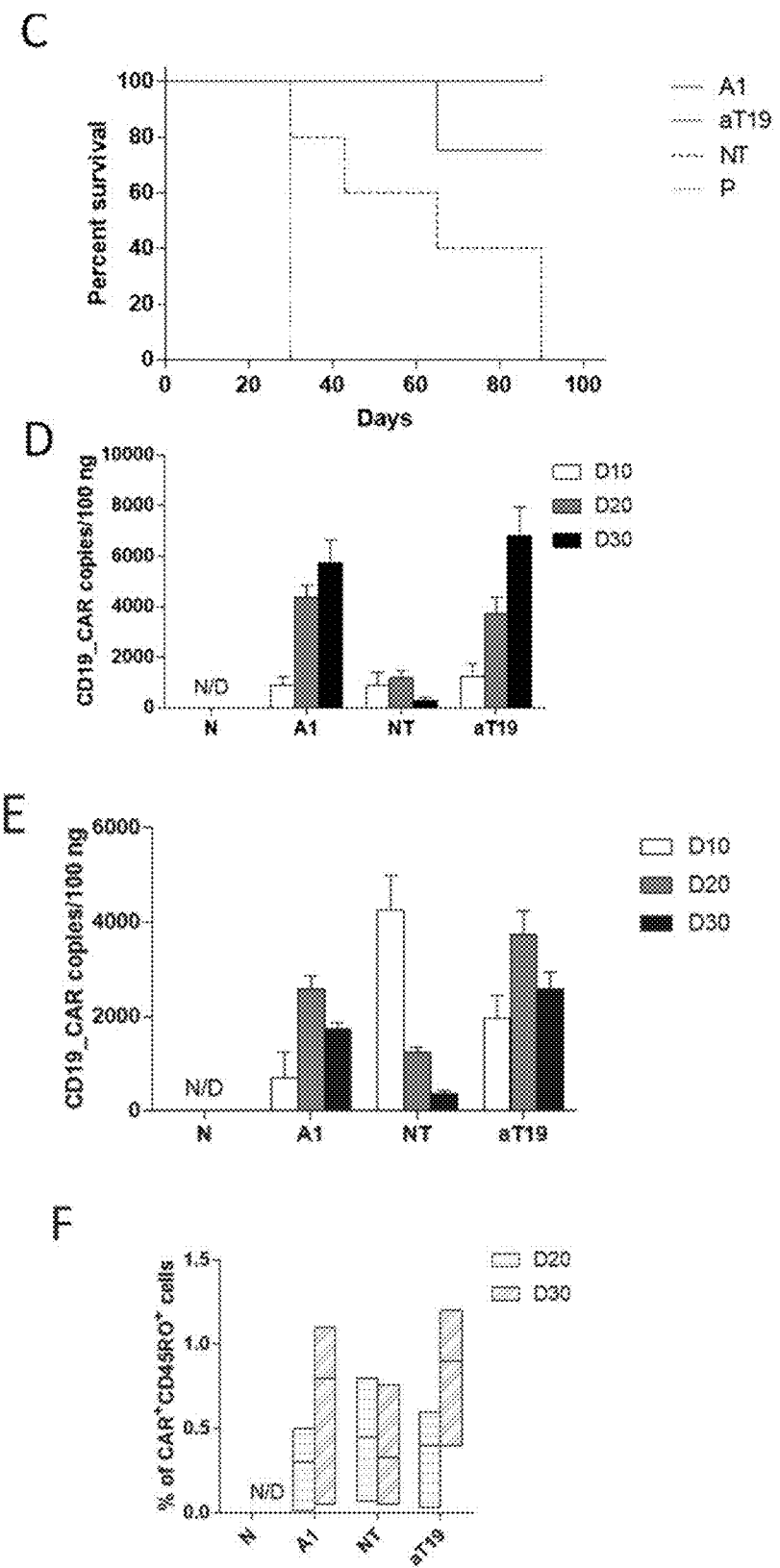

Mice were Treated with CAR-T-19 Cells, and then were Restimulated with aT19 Cells to Increase the Number of CAR+ Cells and the Percentage of CAR+ Memory Cells, and Prolong the Survival Period Raji-Fluc cells are tumor cells with high proliferation capability. Therefore, if a patient receives a stimulating dose of Raji cells, there is a risk that these cells will form tumors. This is obviously unacceptable. Therefore, T cells carrying human CD19 genes (aT19 cells) were used instead of Raji-Fluc cells to restimulate CAR-T-19 cells. The injection time and the number of cells used are listed in Table 4. Mice in the positive/NC group (P and N groups) received tumor cells or only PBS separately. Mice in the group NT received a single dose of CAR-T-19 cells without subsequent doses of stimulating cells. The group A1 was restimulated with Raji-Fluc cells (n=4), while the group aT19 was restimulated with aT19 cells (n=6) (FIG. 8A). In addition, blood was taken from the inner canthus on D10, D20, and D30 (FIG. 8D). The results showed that the survival time of mice in the group aT19 group was significantly longer than that of the NT group. Three mice in the group aT19 survived to D160 (FIG. 8C).

TABLE 4

Dosage of Raji-Fluc or aT19 cells for restimulation

| Time/injection | NC (n = 6) | A1 (n = 4) | NT (n = 5) | aT19 (n = 6) | PC (n = 1) |
|---|---|---|---|---|---|
| D0/Raji-Fluc | / | 5 × 10$^5$ | 5 × 10$^5$ | 5 × 10$^5$ | 5 × 10$^5$ |
| D6/CAR-T | / | 2 × 10$^7$ | 2 × 10$^7$ | 2 × 10$^7$ | / |
| D11/Raji-Fluc or aT19 | / | 5 × 10$^4$ | | 5 × 10$^5$ | / |

In order to clarify that the prolonged survival and delayed tumor recurrence are due to the proliferation of CAR-T-19 cells and subsequent generation of memory CAR-T-19 cells after antigen-positive cell restimulation, qPCR was used to measure the number of CAR copies and flow cytometry was used to measure the percentages of CAR+ and CD45RO+ cells in the peripheral blood and spleen on D10, D20 and D30. The QPCR showed that the number of CAR copies in the blood of mice in the group NT decreased over time (from 1175 copies to 295 copies), while the number of CAR copies in the blood of mice in the group aT19 increased over time (from 1224 copies to 6824 copies), especially after D10 (FIG. 8D). As expected, the percentage of CAR+ cells in the blood of the mice in the group NT decreased (from 3.28% to 0.29%), while the percentage of CAR+ cells in the blood of the mice in the group aT19 increased (from 9.6% to 13.0%) (data not shown). In addition to CAR+ cells, the percentage of CD45RO+ (memory) cells was also measured. As shown in FIG. 8F, the percentage of CAR+CD45RO+ cells in the blood of the group NT decreased slightly from 0.44% (D20) to 0.37% (D30), while the percentage of the blood in the group aT19 increased from 0.34% (D20) to 0.86% (D30), confirming that memory CAR-T-19 cells are generated after restimulation with aT19 cells. In addition, the relationship between CAR+ cells, CD45RO+ cells and total flux (tumor load) in mice was checked. The results show that the total flux is negatively correlated with the number of the two types of cells, indicating that the detection of the number of CAR copies can be used to estimate the residual tumor load.

DISCUSSION

In the past decade, the CAR-T cell therapy has made progress. However, many obstacles have yet to be overcome. Prolonging the efficacy of CAR-T cells in the body and reducing the side effects of CAR-T treatment are the most important. The efficacy of CAR-T cells can be prolonged by using strategies such as optimizing extracellular recognition [19, 20] and CAR-mediated intracellular signal transduction [21] (by adjusting the ratio and type of CAR+ cells) [22] and the simultaneous use of targeted medicine [23]. By adjusting the dose of CAR-T cells and simultaneously using immunosuppressive medicine, the toxicity and side effects [24] related to CAR-T treatment can be reduced. Similar methods have been adopted for vaccines, and are continuously optimized to provide effective protection over a longer period of time while reducing adverse reactions [25]. The most common vaccination protocol involves multiple immunizations or even the use of different immunogens to enhance the immune response. Using the HIV vaccine strategy as an example, the primary and booster immunizations contain viral antigens and nucleic acids respectively, which increase the duration of antibody protection and increase immune activation [26] respectively. However, for the CAR-T cell therapy, multiple vaccinations increase costs and toxicity but reduce efficacy.

In this application, it was surprisingly found that by using cells expressing tumor antigens (such as aT19 cells) for restimulation after CAR-T cell administration, the CAR-T treatment (such as CAR-T-19 treatment) can be optimized by increasing the effective time of cells and reducing their side effects.

The loss of tumor antigens or shorter effectiveness means that tumors tend to recur after CAR-T cell treatment. The loss of tumor antigens is a common immune escape strategy, which is common in ALL. The underlying mechanism involves phenotypic lineage and a switch [27] of alternative splicing. In addition, the number of CAR-T cells needs to be maintained at the minimum level required for long-term tumor control. There are many complicated reasons that make it difficult to maintain the number of CAR-T cells. The reasons include immune response to CAR, cell senescence-induced loss of proliferation capability and activation-induced cell death. By optimizing the structure and conditions used to produce CAR, the immune responses to CAR can be reduced. Since T cell activation and proliferation require continuous immune stimulation, cells carrying tumor antigens are the best stimulating signals for inducing CAR-T cell proliferation. In this application, mice were injected with CAR-T cells on D5 and then exposed to a large dose of tumor (antigen-positive) cells. CAR-T cells proliferated rapidly and killed tumor cells until D9, at which time few tumor cells could be detected in the blood. However, when they are not exposed to antigen-mediated stimulation, the proliferation capability of T cells is reduced. Therefore, it is found that the number of CAR-T cells decreases over time, and ultimately cannot inhibit the proliferation of residual cancer cells. The percentage of CAR+ cells in the blood of mice in the group SNT gradually decreased from D20 to D30. However, if the second "antigen" (that is, aT19 cells) is injected after the cancer cells are almost completely eliminated, CAR-T cells are restimulated and their proliferation capability is maintained. In addition, the results of this application showed that not only the number of CAR+ cells on D30 was significantly higher than that on D20, but also the percentage of CD45RO+ memory cells was significantly higher than that on D20, which further strengthens CAR-T-mediated immunity. Therefore, aT19 cells implement a function like booster immunization. The recurrence-free survival period and overall survival period of mice receiving continuous treatment are better than those of mice receiving single treatment (using CAR-T cells alone), which indicates that continuous immunization may be a safer and more effective strategy to prolong the effective time of CAR-T cells in a clinical environment.

CAR-T treatment may cause cytokine release syndrome (CRS; usually referred to as "cytokine storm") of severe cases, which can be life-threatening 3.28.29.30. This is one of the most serious side effects of CAR-T therapy in addition to off-target effects. CAR-T cells can be activated by tumor cells, and the immune system can be activated by cytokines released by CAR-T cells. If large quantities of inflammatory factors are released, this may lead to fever, hypotension, respiratory distress, multiple organ dysfunction, neuromodulation disorders, and other symptoms 28. CRS usually occurs within the first 2 weeks after CAR-T injection, although the underlying mechanism is unclear. Early intervention with anti-cytokine monoclonal antibodies or glucocorticoids can reduce the risk 31 of CRS. There is evidence showing that the severity of CRS is positively correlated with the number of CAR-T cells inoculated and tumor load 4.22.32.33.34. Herein, through continuous "immunization" with CAR-T cells and then with aT19 cells, continuous immune responses are generated in mice. This can reduce the number of CAR-T cells required for each inoculation and the number of inoculations required over time, thereby reducing the possibility and/or severity of CRS.

The data in this application shows that aT19 cells have clinical utility. This is because these cells are from the same source as CAR-T-19 cells. Clinically, autologous PBMC can be used to generate these cells, which can effectively avoid graft-versus-host diseases. In addition, CAR-T cells recognize aT19 cells through CD19 molecules instead of other immune signals, to ensure specificity. Finally, the aT19 transduction fragment is constructed by replacing the Fab fragment of the CAR antibody with the CD19 gene. This will eliminate any off-target effect in normal tissues in the body. For example, CAR-T-Her2 may attack the epithelium of the lung mucosa and cause pulmonary edema, which can be fatal in severe cases 35. Therefore, from a clinical perspective, continuous "immunization" using aT19 cells should be feasible. In this application, because no tumor was detected on D9, mice were injected with aT19 cells on D10. At this time, the loss of target cells may cause CAR-T cells to attack host tissues. However, the proliferation rate of CAR-T-19 cells may be reduced due to the loss of antigen-specific stimulation, and non-specific host-attack T cells can continue to proliferate. Therefore, aT19 cells were injected on D10 to maintain CAR-T-19 cells.

Clinically, the time of aT19 administration may be adjusted according to the number of CAR-T cells. Herein, the number of CAR-T cells is estimated by measuring the copy number of CAR in the blood through qPCR. The results are consistent with those provided by flow cytometry. In addition, there is a negative correlation between the number of CAR+ cells in the blood sample and the fluorescence value (total flux) (which represents residual tumors in the body). However, the circulatory system in the human body is longer and more complicated than that in mice, and the dose of CAR-T administered clinically is much greater than that given to mice. Therefore, within the first week after CAR-T cell treatment, cancer cells in the human body may not be completely eliminated, and the number of CAR copies in the blood will continue to increase. Subsequently, when the number of CAR+ copies begins to decrease, the number of CAR-T cells gradually decreases and they were replaced by newly generated T cells. At this time, use of aT19 cells for immunization should be considered. Continuous monitoring of the number of CAR+ copies and then timely inoculation of aT19 cells may be a feasible method for clinical application of aT19 cells in this case.

In conclusion, mice treated with CAR-T cells are injected with Raji-Fluc cells, radiated Raji-Fluc cells or aT19 cells. The results show that restimulation of CAR-T cells with live Raji-Fluc cells and aT19 cells improves the recurrence-free survival rate and overall survival rate, while restimulation with radiated (dead) Raji-Fluc cells does not improve the recurrence-free survival rate and overall survival rate. Continuous treatment of aT19 increases the percentages of CAR+ and CD45RO+ cells in the blood, confirming the generation of memory CAR-T cells. This research was supported by the Bio & Medical Technology Development Program of the Korean National Research Foundation funded by the Korean Ministry of Science and Information Technology (No. 2017M3A9C8063523).

REFERENCES

1. Curran E, Stock W. How I treat acute lymphoblastic leukemia in older adolescents and young adults. *Blood* 2015, 125 (24): 3702-3710.
2. Forman S J, Rowe J M. The myth of the second remission of acute leukemia in the adult. *Blood* 2013, 121 (7): 1077-1082.
3. Lee D W, Kochenderfer J N, Stetler-Stevenson M, Cui Y K, Delbrook C, Feldman S A, et al. T cells expressing CD19 chimeric antigen receptors for acute lymphoblastic leukaemia in children and young adults: a phase 1 dose-escalation trial. *Lancet* 2015, 385 (9967): 517-528.
4. Maude S L, Frey N, Shaw P A, Aplenc R, Barrett D M, Bunin N J, et al. Chimeric antigen receptor T cells for sustained remissions in leukemia. *The New England journal of medicine* 2014, 371 (16): 1507-1517.
5. Brentjens R J, Riviere I, Park J H, Davila M L, Wang X, Stefanski J, et al. Safety and persistence of adoptively transferred autologous CD19-targeted T cells in patients with relapsed or chemotherapy refractory B-cell leukemias. *Blood* 2011, 118 (18): 4817-4828.
6. Porter D L, Hwang W T, Frey N V, Lacey S F, Shaw P A, Loren A W, et al. Chimeric antigen receptor T cells persist and induce sustained remissions in relapsed refractory chronic lymphocytic leukemia. *Science translational medicine* 2015, 7 (303): 303ra139.
7. Porter D L, Levine B L, Kalos M, Bagg A, June C H. Chimeric antigen receptor-modified T cells in chronic lymphoid leukemia. *The New England journal of medicine* 2011, 365 (8): 725-733.
8. Kochenderfer J N, Dudley M E, Kassim S H, Somerville R P, Carpenter R O, Stetler-Stevenson M, et al. Chemotherapy-refractory diffuse large B-cell lymphoma and indolent B-cell malignancies can be effectively treated with autologous T cells expressing an anti-CD19 chimeric antigen receptor. *Journal of clinical oncology: official journal of the American Society of Clinical Oncology* 2015, 33 (6): 540-549.
9. Grupp S A, Kalos M, Barrett D. Aplenc R. Porter D L, Rheingold S R, et al. Chimeric antigen receptor-modified T cells for acute lymphoid leukemia. *The New England journal of medicine* 2013, 368 (16): 1509-1518.
10. Park J H, Riviere I, Gonen M, Wang X, Senechal B, Curran K J, et al. Long-Term Follow-up of CD19 CAR Therapy in Acute Lymphoblastic Leukemia. *The New England journal of medicine* 2018, 378 (5): 449-459.
11. Riddell S R, Sommermeyer D, Berger C, Liu L S, Balakrishnan A, Salter A, et al. Adoptive therapy with chimeric antigen receptor-modified T cells of defined subset composition. *Cancer journal* 2014, 20 (2): 141-144.
12. Wang X, Berger C. Wong C W, Forman S J, Riddell S R. Jensen M C. Engraftment of human central memory-derived effector CD8+ T cells in immunodeficient mice. *Blood* 2011, 117 (6): 1888-1898.
13. Berger C. Jensen M C, Lansdorp P M, Gough M, Elliott C, Riddell S R. Adoptive transfer of effector CD8+ T cells derived from central memory cells establishes persistent T cell memory in primates. *The Journal of clinical investigation* 2008, 118 (1): 294-305.
14. Sommermeyer D, Hudecek M, Kosasih P L, Gogishvili T, Maloney D G, Turtle C J, et al. Chimeric antigen receptor-modified T cells derived from defined CD8+ and CD4+ subsets confer superior antitumor reactivity in vivo. *Leukemia* 2016, 30 (2): 492-500.
15. Tae-Wook C. J Shawn J, Punita P, Hallahan C W, Mary M L, Shuying L, et al. Relationship between the size of the human immunodeficiency virus type 1 (HIV-1) reservoir in peripheral blood CD4+ T cells and CD4+: CD8+ T cell ratios in aviremic HIV-1-infected individuals receiving long-term highly active antiretroviral therapy. *Journal of Infectious Diseases* 2002, 185 (11): 1672-1676.
16. RPB. LYH, GCL, CCL, CHR, F Y H, et al. Prevention of perinatally transmitted hepatitis B virus infections with hepatitis B immune globulin and hepatitis B vaccine. *The Lancet* 2014, 384 (9959): 2053-2063.
17. Sabrina K, Qi Z, Michael S, Fran?Ois-Loic C, Els V, Buchholz C J. CD19 and CD20 Targeted Vectors Induce Minimal Activation of Resting B Lymphocytes. *Plos One* 2013, 8 (11): e79047.
18. Loos H, Blok-Schut B, van Doorn R. Hoksbergen R, Brutel de la Riviere A, Meerhof L. A method for the recognition and separation of human blood monocytes on density gradients. *Blood* 1976, 48 (5): 731-742.
19. Grada Z, Hegde M, Byrd T, Shaffer D R, Ghazi A, Brawley V S, et al. TanCAR: A Novel Bispecific Chimeric Antigen Receptor for Cancer Immunotherapy. *Mol Ther Nucleic Acids* 2013, 2: e10$^5$.
20. Ruella M, Barrett D M, Kenderian S S, Shestova O, Hofmann T J, Perazzelli J, et al. Dual CD19 and CD123 targeting prevents antigen-loss relapses after CD19-directed immunotherapies. *J Clin Invest* 2016, 126 (10): 3814-3826.
21. Chmielewski M, Abken H. TRUCKs: the fourth generation of CARs. *Expert Opin Biol Ther* 2015, 15 (8): 1145-1154.
22. Turtle C J, Hanafi L A, Berger C, Gooley T A, Cherian S, Hudecek M, et al. CD19 CAR-T cells of defined CD4+: CD8+ composition in adult B cell ALL patients. *J Clin Invest* 2016, 126 (6): 2123-2138.
23. Cherkassky L, Morello A, Villena-Vargas J, Feng Y, Dimitrov D S, Jones D R, et al. Human CAR T cells with cell-intrinsic PD-1 checkpoint blockade resist tumor-mediated inhibition. *J Clin Invest* 2016, 126 (8): 3130-3144.
24. Gust J, Hay K A, Hanafi L A, Li D, Myerson D, Gonzalez-Cuyar L F, et al. Endothelial Activation and Blood-Brain Barrier Disruption in Neurotoxicity after Adoptive Immunotherapy with CD19 CAR-T Cells. *Cancer Discov* 2017, 7 (12): 1404-1419.
25. Lewis G K, DeVico A L, Gallo R C. Antibody persistence and T-cell balance: two key factors confronting HIV vaccine development. Proceedings of the *National Academy of Sciences of the United States of America* 2014, 111(44): 15614-15621.
26. Day T A, Kublin J G. Lessons learned from HIV vaccine clinical efficacy trials. *Current HIV research* 2013, 11 (6): 441-449.
27. Sotillo E, Barrett D M, Black K L, Bagashev A, Oldridge D, Wu G, et al. Convergence of Acquired Mutations and Alternative Splicing of CD19 Enables Resistance to CART-19 Immunotherapy. *Cancer Discov* 2015, 5 (12): 1282-1295.
28. Bonifant C L, Jackson H J, Brentjens R J, Curran K J. Toxicity and management in CAR T-cell therapy. *Molecular therapy oncolytics* 2016, 3:16011.
29. Davila M L, Riviere I, Wang X, Bartido S, Park J, Curran K, et al. Efficacy and toxicity management of 19-28z CAR T cell therapy in B cell acute lymphoblastic leukemia. *Science translational medicine* 2014, 6 (224): 224ra225.
30. Lee D W, Gardner R, Porter D L, Louis C U, Ahmed N, Jensen M, et al. Current concepts in the diagnosis and management of cytokine release syndrome. *Blood* 2014, 124 (2): 188-195.
31. Turtle C J, Hanafi L A, Berger C, Hudecek M, Pender B. Robinson E, et al. Immunotherapy of non-Hodgkin's lymphoma with a defined ratio of CD8+ and CD4+CD19-specific chimeric antigen receptor-modified T cells. *Science translational medicine* 2016, 8 (355): 355ra116.
32. Park J H, Geyer M B, Brentjens R J. CD19-targeted CAR T-cell therapeutics for hematologic malignancies: interpreting clinical outcomes to date. *Blood* 2016, 127 (26): 3312-3320.
33. Geyer M B, Brentjens R J. Review: Current clinical applications of chimeric antigen receptor (CAR) modified T cells. *Cytotherapy* 2016, 18 (11): 1393-1409.
34. Grupp S A, Kalos M, Barrett D. Aplenc R, Porter D L, Rheingold S R, et al. Chimeric antigen receptor-modified T cells for acute lymphoid leukemia. *The New England journal of medicine* 2013, 368 (16): 1509-1518.
35. Morgan R A. Yang J C, Kitano M, Dudley M E, Laurencot C M, Rosenberg S A. Case report of a serious adverse event following the administration of T cells transduced with a chimeric antigen receptor recognizing ERBB2. *Molecular therapy: the journal of the American Society of Gene Therapy* 2010, 18 (4): 843-851.

What we claimed is:

1. A method for treating CD19-expressing cancer in a subject or for preventing CD19-expressing cancer progression or recurrence in a subject, comprising the following steps:
   (a) administering therapeutic T cells specifically targeting a cancer-related antigen to the subject; and
   (b) administering cells expressing the cancer-related antigen to the subject,
   wherein the cells expressing CD19 are non-irradiated living cells expressing CD19,
   wherein the therapeutic T cells are T cells (CAR-T cells) comprising a chimeric antigen receptor (CAR) specifically targeting CD19,
   wherein the cells expressing CD19 are administered after the administration of the therapeutic T cells.

2. The method according to claim 1, wherein the therapeutic T cells are administered one or more times.

3. The method according to claim 1, wherein the cells expressing CD19 are administered one or more times.

4. The method according to claim 1, wherein the cells expressing CD19 are administered 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, or 20 days after the therapeutic T cells are administered.

5. The method according to claim 1, wherein the cells expressing CD19 are administered after the cancer cell load is reduced by administration of the therapeutic T cells.

6. The method according to claim 5, wherein after the cancer cell load is reduced by at least about 5%, at least about 10%, at least about 20%, at least about 30%, at least about 40%, at least about 50%, at least about 60%, at least about 70%, at least about 80%, or at least about 90%, the cells expressing CD19 are administered.

7. The method according to claim 1, wherein after the cancer is completely remitted by administering the therapeutic T cells, the cells expressing CD19 are administered.

8. The method according to claim 1, wherein about $10^4$ to about $10^9$ therapeutic T cells are administered.

9. The method according to claim 1, wherein about $10^3$ to about $10^6$ cells expressing CD19 are administered.

10. The method according to claim 1, wherein the CAR comprises an extracellular antigen binding domain that specifically binds to CD19, a CD8α hinge and a transmembrane domain, a CD3ζ signal transduction domain, and a 4-1BB costimulatory domain.

11. The method according to claim 1, wherein the cells expressing CD19 are not cancer cells.

12. The method according to claim 11, wherein CD19 is expressed on the surface of the living cells.

13. The method according to claim 1, wherein the cells expressing CD19 are derived from immune cells.

14. The method according to claim 1, wherein the therapeutic T cells and/or the cells expressing CD19 are derived from autologous cells of the subject.

15. The method according to claim 1, wherein the therapeutic T cells and/or the cells expressing CD19 are derived from allogeneic cells.

16. The method according to claim 1, wherein the subject has undergone cancer treatment using therapeutic T cells specifically targeting CD19.

17. The method according to claim 1, wherein the cancer is selected from lymphoma, hematological malignancies, Hodgkin's disease, non-Hodgkin's lymphoma acute myeloid leukemia, chronic myeloid leukemia, acute lymphocytic leukemia, chronic lymphocytic leukemia, lymphocytic lymphoma, primary central nervous system (CNS) lymphoma, T cell lymphoma, and B-cell acute lymphoblastic leukemia (B-ALL), and combinations of these cancers.

* * * * *

SEQUENCE LISTING

<160> NUMBER OF SEQ ID NOS: 5

<210> SEQ ID NO 1
<211> LENGTH: 486
<212> TYPE: PRT
<213> ORGANISM: Artificial Sequence
<220> FEATURE:
<223> OTHER INFORMATION: CD19-CAR  amino acid sequence

<400> SEQUENCE: 1

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

```
Ser Ala Ser Leu Gly Asp Arg Val Thr Ile Ser Cys Arg Ala Ser Gln
            35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445
```

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
            485

<210> SEQ ID NO 2
<211> LENGTH: 1458
<212> TYPE: DNA
<213> ORGANISM: Artificial Sequence
<220> FEATURE:
<223> OTHER INFORMATION: CD19-CAR encoding sequence

<400> SEQUENCE: 2

| | | | |
|---|---|---|---|
| atggccttac cagtgaccgc cttgctcctg ccgctggcct tgctgctcca cgccgccagg | | | 60 |
| ccggacatcc agatgacaca gactacatcc tccctgtctg cctctctggg agacagagtc | | | 120 |
| accatcagtt gcagggcaag tcaggacatt agtaaatatt taaattggta tcagcagaaa | | | 180 |
| ccagatggaa ctgttaaact cctgatctac catacatcaa gattacactc aggagtccca | | | 240 |
| tcaaggttca gtggcagtgg gtctggaaca gattattctc tcaccattag caacctggag | | | 300 |
| caagaagata ttgccactta cttttgccaa cagggtaata cgcttccgta cacgttcgga | | | 360 |
| ggggggacca agctggagat cacaggtggc ggtggctcgg gcggtggtgg gtcgggtggc | | | 420 |
| ggcggatctg aggtgaaact gcaggagtca ggacctggcc tggtggcgcc ctcacagagc | | | 480 |
| ctgtccgtca catgcactgt ctcagggtc tcattacccg actatggtgt aagctggatt | | | 540 |
| cgccagcctc cacgaaaggg tctggagtgg ctgggagtaa tatggggtag tgaaaccaca | | | 600 |
| tactataatt cagctctcaa atccagactg accatcatca aggacaactc caagagccaa | | | 660 |
| gttttcttaa aaatgaacag tctgcaaact gatgacacag ccatttacta ctgtgccaaa | | | 720 |
| cattattact acggtggtag ctatgctatg gactactggg gccaaggaac ctcagtcacc | | | 780 |
| gtctcctcaa ccacgacgcc agcgccgcga ccaccaacac cggcgcccac catcgcgtcg | | | 840 |
| cagcccctgt ccctgcgccc agaggcgtgc cggccagcgg cggggggcgc agtgcacacg | | | 900 |
| agggggctgg acttcgcctg tgatatctac atctgggcgc ccttggccgg acttgtgggg | | | 960 |
| gtccttctcc tgtcactggt tatcacccct tactgcaaac ggggcagaaa gaaactcctg | | | 1020 |
| tatatattca acaaccatt tatgagacca gtacaaacta tcaagagga agatggctgt | | | 1080 |
| agctgccgat ttccagaaga agaagaagga ggatgtgaac tgagagtgaa gttcagcagg | | | 1140 |
| agcgcagacg cccccgcgta ccagcagggc cagaaccagc tctataacga gctcaatcta | | | 1200 |
| ggacgaagag aggagtacga tgttttggac aagagacgtg gccgggaccc tgagatgggg | | | 1260 |
| ggaaagccga aggaagaa cctcaggaa ggcctgtaca tgaactgca gaaagataag | | | 1320 |
| atggcggagg cctacagtga gattgggatg aaaggcgagc gccggagggg caaggggcac | | | 1380 |
| gatggccttt accagggtct cagtacagcc accaaggaca cctacgacgc ccttcacatg | | | 1440 |
| caggccctgc cccctcgc | | | 1458 |

<210> SEQ ID NO 3
<211> LENGTH: 25
<212> TYPE: DNA
<213> ORGANISM: Artificial Sequence
<220> FEATURE:
<223> OTHER INFORMATION: CD19 4-1BB F primer

<400> SEQUENCE: 3

```
tgccgatttc cagaagaaga agaag                                                25

<210> SEQ ID NO 4
<211> LENGTH: 18
<212> TYPE: DNA
<213> ORGANISM: Artificial Sequence
<220> FEATURE:
<223> OTHER INFORMATION: CD19 4-1BB R primer

<400> SEQUENCE: 4
gcgctcctgc tgaacttc                                                        18

<210> SEQ ID NO 5
<211> LENGTH: 19
<212> TYPE: DNA
<213> ORGANISM: Artificial Sequence
<220> FEATURE:
<223> OTHER INFORMATION: CD19 4-1BB MGB probe

<400> SEQUENCE: 5
actctcagtt cacatcctc                                                       19
```